US008951795B2

(12) United States Patent
Mizukami et al.

(10) Patent No.: US 8,951,795 B2
(45) Date of Patent: Feb. 10, 2015

(54) REVASCULARIZATION CELLS DERIVED FROM MONONUCLEAR CELLS, AND METHOD OF INDUCING DIFFERENTIATION THEREOF

(75) Inventors: Yusuke Mizukami, Hokkaido (JP); Junpei Sasajima, Hokkaido (JP); Yoshiaki Sugiyama, Hokkaido (JP); Kazuya Sato, Hokkaido (JP); Yutaka Kohgo, Hokkaido (JP)

(73) Assignee: National University Corporation Asahikawa Medical University, Hokkaido (JP)

( * ) Notice: Subject to any disclaimer, the term of this patent is extended or adjusted under 35 U.S.C. 154(b) by 402 days.

(21) Appl. No.: 13/138,835

(22) PCT Filed: Mar. 29, 2010

(86) PCT No.: PCT/JP2010/002254
§ 371 (c)(1),
(2), (4) Date: Dec. 12, 2011

(87) PCT Pub. No.: WO2010/116665
PCT Pub. Date: Oct. 14, 2010

(65) Prior Publication Data
US 2012/0100610 A1 Apr. 26, 2012

(30) Foreign Application Priority Data
Apr. 7, 2009 (JP) ................................. 2009-093459

(51) Int. Cl.
*C12N 5/00* (2006.01)
*C12N 5/078* (2010.01)
*A61K 35/12* (2006.01)

(52) U.S. Cl.
CPC ......... *C12N 5/0634* (2013.01); *A61K 2035/124* (2013.01); *C12N 2501/105* (2013.01); *C12N 2501/11* (2013.01); *C12N 2501/115* (2013.01); *C12N 2501/145* (2013.01); *C12N 2501/165* (2013.01); *C12N 2501/22* (2013.01); *C12N 2501/26* (2013.01)
USPC .......................................... 435/377; 435/375

(58) Field of Classification Search
USPC ................................. 435/377, 375
See application file for complete search history.

(56) References Cited

U.S. PATENT DOCUMENTS

2008/0070830 A1 3/2008 Dzau et al.

FOREIGN PATENT DOCUMENTS

| JP | 2001-503427 A | 3/2001 |
|---|---|---|
| JP | 2002-020298 A | 1/2002 |
| JP | 2008-266220 A | 11/2008 |
| JP | 2009-055817 A | 3/2009 |
| WO | 98-19712 A1 | 5/1998 |
| WO | 2004-063365 A1 | 7/2004 |
| WO | 2006-090882 A1 | 8/2006 |
| WO | 2007/099534 A2 | 9/2007 |
| WO | 2008-142862 A1 | 11/2008 |

OTHER PUBLICATIONS

Muller et al. (The role of PECAM-1 (CD31) in leukocyte emigration: studies in vitro and in vivo. Journal of Leukocyte Biology. 1995 57: 523-528).*
Kubo et al. (Leukocyte CD11b expression is not essential for the development of atherosclerosis in Mice. Journal of Lipid Research. 2000 41:1060-1066).*
Eash et al. (CXCR4 is a key regulator of neutrophil release from the bone marrow under basal and stress granulopoiesis conditions. Blood 2009 113: 4711-4719).*
Christophersson et al. Clinical and Experimental Pancreatic Islet Transplantation to Striated Muscle. Diabetes (2010) 59:2569-2576.*
Hoenig Michael R et al: "Hypoxia inducible factor-1 alpha, endothelial progenitor cells, monocytes, cardiovascular risk, wound healing, cobalt and hydralazine: A unifying hypothesis", Current Drug Targets, Bentham Science Publisher, US, vol. 9, No. 5, May 1, 2008, pp. 422-435.
Gupta Shalley Kant et al: "SDF-1alpha modulates adhesion molecule expression in monocytic leukemia cells and binding to human aortic endothelial cells", FASEB Journal, Fed. of American Soc. For Experimental Biology, US, vol. 15, No. 4, Mar. 7, 2001, p. A334.
Jia J et al: "Human monocyte-derived hemangioma-like endothelial cells: evidence from an in vitro study", Cardiovascular Pathology, Elsevier Science, New York, NY, US, vol. 17, No. 4, Jul. 1, 2008, pp. 212-218.
Zhang R et al: "Acceleration of endothelial-like cell differentiation from CD14+ monocytes in vitro", Experimental Hematology, Elsevier Inc., US, vol. 33, No. 12, Dec. 1, 2005, pp. 1554-1563.
European Search Report for EP10761371 dated Jan. 30, 2013.
International Search Report for PCT/JP2010/002254; Jun. 22, 2010.
International Preliminary Report for PCT/JP2010/002254; Nov. 24, 2011.
Il, M., et al. "Endothelial Progenitor Thrombospondin-1 Mediates Diabetes-Induced Delay in Reendothelialization Following Arterial Injury." In: Circulation Research, vol. 98; 2006; pp. 697-704.

(Continued)

*Primary Examiner* — Karen Cochrane Carlson
*Assistant Examiner* — Natalie Moss
(74) *Attorney, Agent, or Firm* — Pearne & Gordon LLP

(57) ABSTRACT

The present invention relates to a method of safely and simply inducing differentiation of mononuclear cells into cells that promote neovascular stabilization and maturation, and lead to recovering from ischemia or tissue repair. The cells according to the present invention are obtained by inducing differentiation of a mononuclear cell by culturing the mononuclear cell in a medium (particularly a serum-free medium) containing one or more selected from vascular endothelial growth factor (VEGF), basic fibroblast growth factor (bFGF), thrombopoietin (TPO), granulocyte-colony stimulating factor (G-CSF) and FMS-like tyrosine kinase 3 ligand (FLT3L), and collecting a cell population expressing CD11b.

19 Claims, 26 Drawing Sheets
(3 of 26 Drawing Sheet(s) Filed in Color)

(56) References Cited

OTHER PUBLICATIONS

Chang, E.I., et al. "Age Decreases Endothelial Progenitor Cell Recruitment Through Decreases in Hypoxia-Inducible Factor 1α Stabilization During Ischemia." In: Circulation, vol. 116; 2007; pp. 2818-2829.

Gulati, R., et al. "Diverse Origin and Function of Cells With Endothelial Phenotype Obtained From Adult Human Blood." In: Circulation Research, vol. 93; 2003; pp. 1023-1025.

Asahara, T., et al. "Isolation of Putative Progenitor Endothelial Cells for Angiogenesis." In: Science, vol. 275; Feb. 14, 1997; pp. 964-967.

Yamazaki, M., et al. "Sonic hedgehog derived from human pancreatic cancer cells augments angiogenic function of endothelial progenitor cells." In: Cancer Science, vol. 99, No. 6; Jun. 2008; pp. 1131-1138.

Kalka, C., et al. "Transplantation of ex vivo expanded endothelial progenitor cells for therapeutic neovascularization." In: PNAS (Proc Natl Acad Sci), vol. 97, No. 7; Mar. 28, 2000; pp. 3422-3427.

Assmus, B., et al. "Transplantation of Progenitor Cells and Regeneration Enhancement in Acute Myocardial Infarction (Topcare-AMI)." In: Circulation, vol. 106; 2002; pp. 3009-3017.

Murohara, T. "The 104th Annual Meeting of the Japan Internal Medicine Society, Symposium , 3. Possibility and limits of cellular therapy, 3) Current status and prospect of revascularization therapy." In: Internal Medicine, vol. 96, No. 9; 2007; pp. 129-136.

Kubo, M., et al. "Hypoxic preconditioning increases survival and angiogenic potency of peripheral blood mononuclear cells via oxidative stress resistance." In: AJP—Heart and Circulatory Physiology, vol. 294; 2008; pp. H590-H595.

Kerbel, R.S. "Molecular Origins of Cancer: Tumor Angiogenesis." Review article. In: New England Journal of Medicine, vol. 358, No. 19; May 8, 2008; pp. 2039-2049.

Yamada, Y., et al. "Physiological pathway of differentiation of hematopoietic stem cell population into mural cells." In: The Journal of Experimental Medicine, vol. 203, No. 4; Apr. 17, 2006; pp. 1055-1065.

Yurugi-Kobayashi, T., et al. "Effective contribution of transplanted vascular progenitor cells derived from embryonic stem cells to adult neovascularization in proper differentiation stage." In: Blood, vol. 101, No. 7; Apr. 1, 2003; pp. 2675-2678.

Yang, L., et al. "Expansion of myeloid immune suppressor Gr+CD11b+ cells in tumor-bearing host directly promotes tumor angiogenesis." In: Cancer Cell, vol. 6; Oct. 2004; pp. 409-421.

De Palma, M., et al. "Tie2 identifies a hematopoietic lineage of proangiogenic monocytes required for tumor vessel formation and a mesenchymal population of pericyte progenitors." In: Cancer Cell, vol. 8; Sep. 2005; pp. 211-226.

Rehman, J., et al. "Peripheral Blood 'Endothelial Progenitor Cells' Are Derived From Monocyte/Macrophages and Secrete Angiogenic Growth Factors." In: Circulation, vol. 107; 2003; pp. 1164-1169.

Leukocyte—New World Encyclopedia, http://www.newworldencyclopedia.org/entry/Leukocyte, Mar. 31, 2014, pp. 1-6.

Flow Cytometry—Gates and Regions, http://www.abdserotec.com/flow-cytometry-gates-regions.html, AbD Serotec, A Bio-Rad Company, Mar. 31, 2014, pp. 1-2.

Histopaque—1077 Production Information Sheet, http://www.sigmaaldrich.com/content/dam/sigma-aldrich/docs/Sigma/Product_Information_Sheet/1/10771pis.pdf, Sigma-Aldrich, Feb. 12, 2014.

Kawamoto, et al., Ex vivo activation of angiogenic property in human peripheral blood-derived monocytes by thrombopoietin, Int J Hematol, 98: 417-429, Springer, Sep. 4, 2013.

Nozawa, et al., Infiltrating neutrophils mediate the initial angiogenic switch in a mouse model of multistage carcinogenesis, Proceedings of the National Academy of Sciences, USA, vol. 103, No. 33, 12493-12498, The National Academy of Sciences, Aug. 15, 2006.

Lodish, et al., Chapter 3: Protein Structure and Function, in Molecular Cell Biology (5th Edition), title page, copyright page, and pp. 59-99, W.H. Freeman and Company, 2004.

Fan, Y. et al., "Endothelial Progenitor Cell Transplantation Improves Long-Term Stroke Outcome in Mice," Ann. Neurol. vol. 67, pp. 488-497 (Apr. 2010), American Neurological Society.

Office action in European Appl. No. 10761371.3-1402, mailed Sep. 9, 2014.

\* cited by examiner

Fig. 2-1
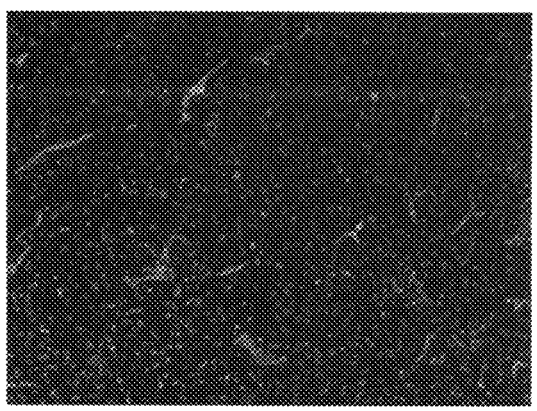
Control
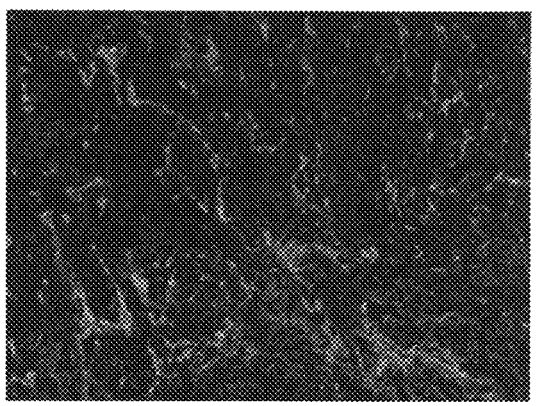
Cultured mononuclear cell transplantation
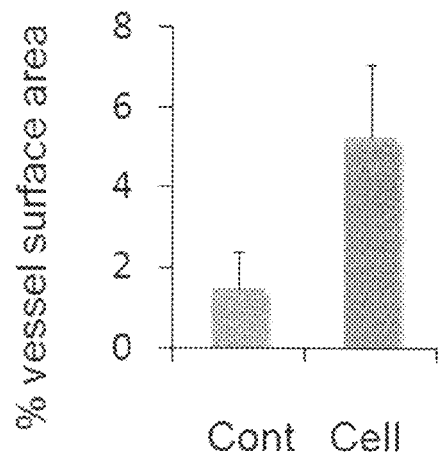
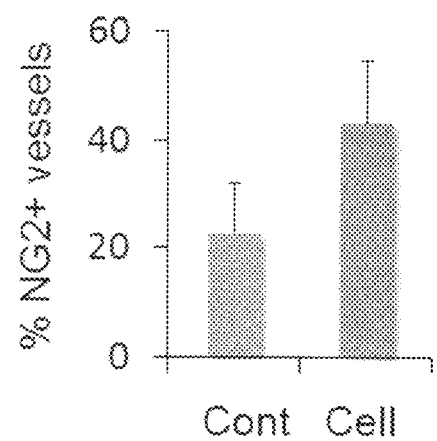
Fig. 2-2
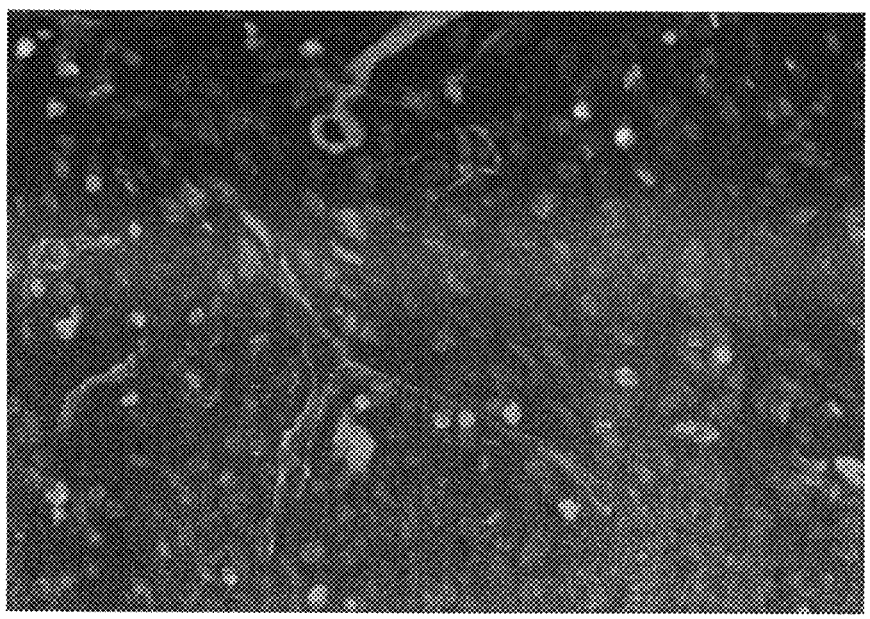

All mononuclear cells | CD11b-negative mononuclear cells | CD11b-positive mononuclear cells

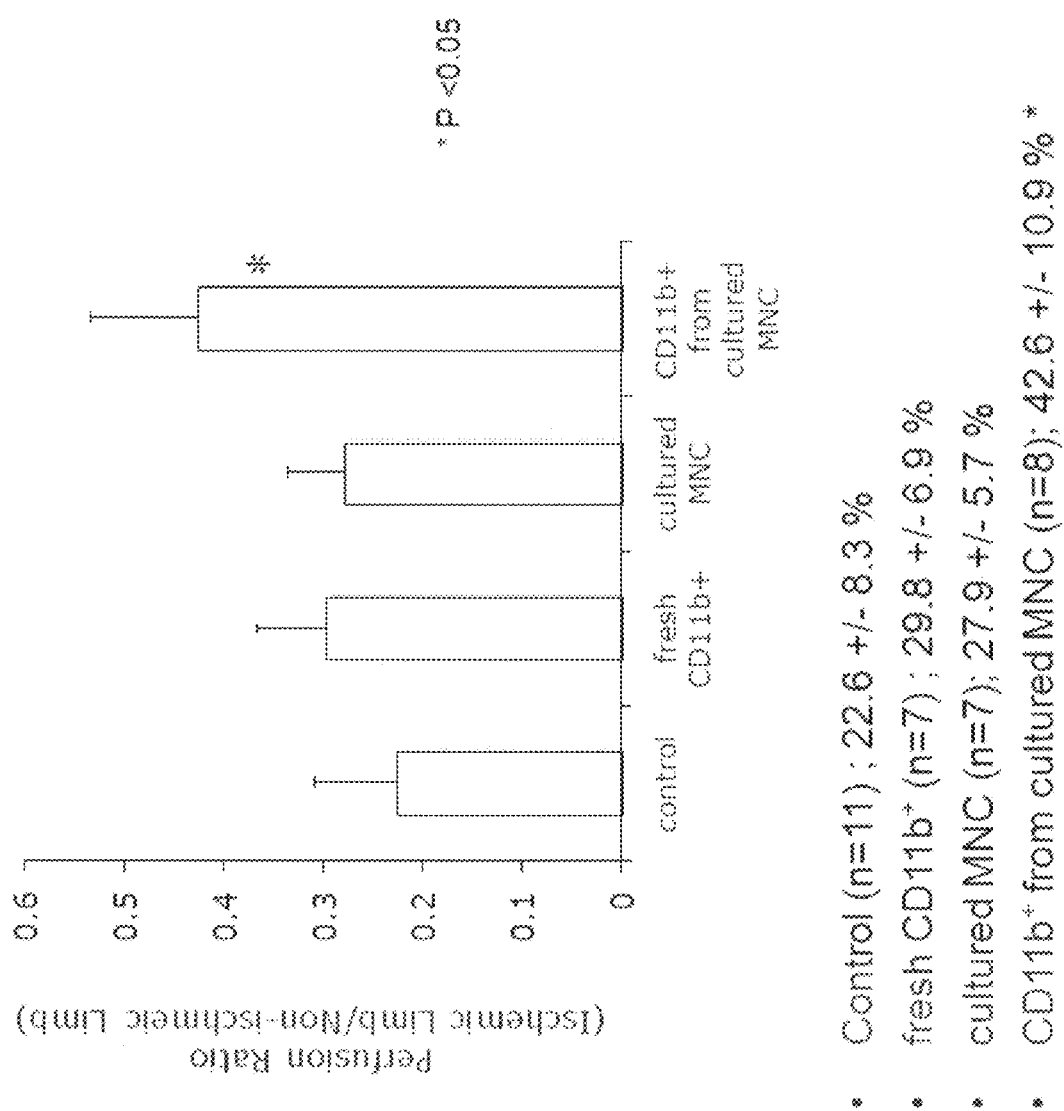

REVASCULARIZATION CELLS DERIVED FROM MONONUCLEAR CELLS, AND METHOD OF INDUCING DIFFERENTIATION THEREOF

TECHNICAL FIELD

The present invention relates to a new revascularization cell population derived from a mononuclear cell population and a method of inducing differentiation thereof. More specifically, the present invention relates to a new revascularization cell population that is derived from mononuclear cells, and that promote neovascular stabilization and maturation, and lead to recovering from ischemia or tissue repair, and to a safe and simple method of inducing differentiation thereof.

BACKGROUND ART

In the treatment of various ischemia-related diseases associated with arteriosclerosis, the revascularization treatment by local or transvenous transplantation of autologous myeloblasts (mononuclear cells) has been provided as an advanced medical technique. Under current situation, it is thought that in most cases fractions containing hematopoietic stem cells such as CD34-positive cells and CD133-positive cells have anti-ischemia effects (see Patent Literature 1), and therefore the improvement of therapeutic performance by purification of cells with these surface antigens is anticipated. Though bone marrow and umbilical cord blood may become a source of such cells, as they contain relatively many undifferentiated cells, peripheral blood contains very few CD34-positive cells and CD133-positive cells. Therefore, when peripheral blood is used, large scale mobilization of bone marrow progenitor cells by granulocyte colony-stimulating factor (G-CSF) etc. is commonly practiced, and still, collecting enough number of cells required for a certain therapeutic effect can be difficult.

As for patients with pre-existing diseases such as arteriosclerosis or diabetes and elderly people, in addition to the difficulty in collecting bone marrow, a concern exists about declines of the cellular function itself (see Non Patent Literatures 1 and 2). As a new approach, a method using ex vivo amplification of progenitor cells contained in umbilical cord blood has been reported (see Patent Literature 2). Furthermore, the utilization of embryonic stem cells (ES cells) or induced pluripotent stem cells (iPS cells) is anticipated as a future source of such undifferentiated cells (stem cells). However, there is still a long way to the realization thereof.

There is a report suggesting the use of endothelial progenitor cells (EPCs) obtained by inducing differentiation of mononuclear cells contained in bone marrow or peripheral blood (see Non Patent Literature 3), in contrast to methods using rare (hematopoietic) stem cells as a source in the revascularization treatment. In this report, mononuclear cells are cultured in a medium, such as EBM2, that contains cytokines including vascular endothelial growth factor (VEGF) and that is optimized for culturing vascular endothelial cells, and the cells collected as adherent cells or floating cells are called EPCs.

Adherent cells obtained by inducing differentiation of murine peripheral blood or bone marrow mononuclear cells in EGM2-MV medium supplemented with 10% FBS, in a culture dish treated with rat vitronectin uptake acetylated low-density lipoprotein (acetylated LDL) and show affinity for lectin. Among the adherent cells, cells in fusiform shape and cells in round shape are mixed. The proportion of the former is higher within the first week of culturing, while with longer culturing cells in pavement shape grow densely, which are deduced to be derived from the latter. Thus, the adherent cells obtained by the method described above include distinct cell populations, it is reasonable to consider that EPCs are included in the latter fraction. However, the occurrence of subculturable cells from pavement-shaped colonization is very low. Fusiform cells seen abundant in the initial stage of the differentiation-inducing culture swell and extend, and decline substantially in their survival rate.

Transplanting (local and systemic administration) cells obtained by culturing mouse mononuclear cells for a short period of about 1 week into an small animal, such as mouse, that suffers from myocardial or lower limb ischemia is known to lead to recovering from ischemia. Namely, it is known that (a population of) cells obtained by inducing differentiation of mononuclear cells have an effect to promote vascularization. On the other hand, it is also known that cells (cell populations) obtained by inducing differentiation of mononuclear cells have a reduction effect of the hypoxia region of tumor (cancer) tissue (see Patent Literature 3) and liver fibrosis suppression effects (see Patent Literature 4). However, these cells do not necessarily express the antigens called EPC markers (see Non Patent Literature 4), such as CD34 and VEGF receptor 2 (VEGFR2/Flk-1/KDR) on the cell membrane. It is not clear whether these cells have lost the stem cell antigens during the differentiation process of hematopoietic stem cells, or they are of a population of cells derived from non-hematopoietic stem cells that do not express the stem cell antigens from the beginning.

Similarly, it has been reported that in a culture period of about 1 week, adherent cells obtained by differentiation-inducing culture of human peripheral blood mononuclear cells in EGM2-MV medium supplemented with 10% FBS, in a culture dish treated with human fibronectin keep round-to-fusiform shapes well, have the ability to promote lumen formation of human vascular endothelial cells such as HUVEC (see Non Patent Literature 5), and suppress necrosis associated with lower limb ischemia in a nude mouse (see Non Patent Literature 6). Also reported are clinical trial results showing that autotransplantation of human peripheral blood mononuclear cells treated with similar differentiation induction improved cardiac function after myocardial infarction, and transplanted cells are defined as EPCs expressing surface antigens such as Flk-1, CD31, CD105, VE-cadherin (see Non Patent Literature 7). However, because the culture period was as short as 3 days, amplification of hematopoietic stem cells in large quantities is reasonably deduced to be rather unlikely, and the possibility that they were cells derived from monocyte line is undeniable.

With long-term culture with inducing differentiation of mononuclear cells, whether cells of interest will be efficiently obtained, or whether cellular functions and the quality of the cells will be kept well is not clear yet. Although hypoxia environments are known to keep EPCs in undifferentiated states (see Non Patent Literature 8), and to have the antioxidant effect (see Non Patent Literature 9) during the induction of differentiation. Because EGM2-MV media containing FBS were used in most of reports so far, they are not directly applicable to clinical applications (administration to human).

The induction of differentiation of mononuclear cells as a source into EPCs having the ability to differentiate into vascular endothelial cells is anticipated as an alternative method of the revascularization treatment with CD34 or CD113-positive hematopoietic stem cells. However, as noted above, (a population of) adherent cells obtained by inducing differentiation of mononuclear cells are of a heterogenous population(s). A clinically applicable technique for efficiently obtaining only EPCs suitable for revascularization treatment by differentiation induction has not been established yet.

CD11b is one of the hemocyte differentiation antigens that are expressed mainly in monocytes and lymphocytes. CD11b-positive cells include some of cells that are responsible for immunological surveillance and lymphocytes, such as macrophages, dendritic cells, natural killer cells (NK cells). On the other hand, it is also known that in abnormal new blood vessels seen in cancer or like, the expression of a receptor for an angiogenic factor, such as VE-cadherin, VEGF receptor 1 (VEGFR1), SDF-1 receptor (CXCR4), and angiopoietin-1 receptor (Tie-2), together with CD11b antigen is found. Thus, the possibility that non-stem cells expressing these markers may have an important role in vascularization, for example, via differentiating into cells having a vascularization promoting effect is suggested (see Non Patent Literature 10).

On the other hand, CD11b-positive cells include also relatively undifferentiated fractions. It is reported that a part of CD11b-positive cells in bone marrow can differentiate into CD31 antigen-positive vascular endothelial cells or smooth muscle actin (SMA) antigen-positive parietal cells in the presence of an angiogenic factor, such as vascular endothelial growth factor (VEGF), platelet-derived growth factor (PDGF) or the like (see Non Patent Literature 11). In addition, relatively young cells, such as vascular progenitor cells (VPC) obtained by inducing differentiation of embryonic stem cells (see Non Patent Literature 12) are thought to have properties similar to these, and their ultimate direction of differentiation may depend on the environment.

The facts described above suggest the possibility that some CD11b-positive cells directly become neovascular components, or they are indirectly involved in the promotion of angiogenesis or the stabilization of new blood vessels through cytokine production. However, a differentiation induction system that is free from samples derived from animal, such as fetal bovine serum (FBS, FCS), for inducing differentiation into cells with the functions such as revascularization, angioplasty, blood vessel stabilization, using, as a source, non-hematopoietic stem cells expressing monocyte differentiation markers such as CD11b, which are relatively abundant in mononuclear cells has not yet established. Moreover, cells that express monocyte markers such as CD11b may differentiate into endothelial cells in tumor vessels (see Non Patent Literature 13), and also may locate around blood vessels without differentiating into vascular endothelial cells (for example, CD11b-positive cells coexpressing Tie2; see Non Patent Literature 14); and practically it is difficult to distinguish their characteristics and roles strictly in a body with tumor (cancer) (see Non Patent Literature 15). Thus, it is not clear whether cells obtained by inducing differentiation of CD11b expression mononuclear cells function as EPCs in the end.

CITATION LIST

Patent Literature

Patent Literature 1: National Publication of International Patent Application No. 20.01-503427
Patent Literature 2: WO2006/90882
Patent Literature 3: WO2008/142862
Patent Literature 4: Japanese Patent Laid-Open No. 2008-266220

Non Patent Literature

Non Patent Literature 1: Ii M, et al: Circ Res 98, 697-704, 2006
Non Patent Literature 2: Chang E I, et al: Circulation 116, 2818-2829, 2007
Non Patent Literature 3: Gulati R, et al: Circ Res 93, 1023-1025, 2003
Non Patent Literature 4: Asahara T, et al: Science 275, 964-967, 1997
Non Patent Literature 5: Yamazaki M, et al: Cancer Sci 99, 1131, 2008
Non Patent Literature 6: Kalka C, et al: PNAS 97, 3422-7, 2000
Non Patent Literature 7: Assmus B, et al: Circulation 106, 3009-3017, 2002
Non Patent Literature 8: The 104 th Annual Meeting of the Japan Internal Medicine Society, Symposium, 3. Possibility and limits of cellular therapy, 3) Current status and prospect of revascularization therapy. Internal Medicine Vol. 96, No. 9, pp 29-136, 2007
Non Patent Literature 9: Kubo M, et al: Am J Physiol heat Circ Physiol 294, H590-5, 2008
Non Patent Literature 10: Karbel R S. N Engl J Med 358, 2039-49, 2008
Non Patent Literature 11: Yamada T, Takakura N. JEM 203, 1055-65, 2006
Non Patent Literature 12: Yurugi-Kobayashi T, et al.: Blood 101, 2675-2678, 2003
Non Patent Literature 13: Yang L, et al: Cancer Cell 6, 409-421, 2004
Non Patent Literature 14: De Plama M, et al.: Cancer Cell 8, 211-226, 2005
Non Patent Literature 15: Rehman J, et al.: Circulation 107, 1164-169, 2003

SUMMARY OF INVENTION

Technical Problem

An object of the present invention is to establish technique for inducing differentiation of mononuclear cells safely and easily into cells that promote neovascular stabilization and maturation and lead to ischemia and tissue repair, as an alternative to quantitatively limited CD34-positive or CD133-positive hematopoietic stem cells to provide novel means of revascularization treatment.

Solution to Problem

The inventors studied diligently to solve the problem, and succeeded in obtaining intended cells by inducing differentiation of (a population of) cells mainly including monocyte and lymphocyte fractions, which are relatively abundant in peripheral blood, particularly, by inducing differentiation of some of CD11b-positive cells.

The obtained cells did not differentiate into vascular endothelial cells directly, but they promoted revascularization and lead to recovering from ischemia and tissue repair by promoting neovascular stabilization and maturation. In other words, when systemically administered to a body with an ischemic zone such as cancer, they distributed around new blood vessels and promoted vascular stabilization and maturation. Moreover, this cell expressed CD11b in addition to CD31 and CXCR4 and slightly expressed a surface antigen of c-Kit as well. From the above characteristics, it was suggested that cells obtained by inducing differentiation of mononuclear cells are (a population of) cells belonging to a class different from cells conventionally defined as EPCs.

Thus, the present invention relates to a cell population expressing CD11b, obtained by inducing differentiation of a mononuclear cell population by culturing the mononuclear cell population in a medium containing one or more selected from vascular endothelial growth factor (VEGF), basic fibroblast growth factor (bFGF), thrombopoietin (TPO), granulocyte-colony stimulating factor (G-CSF) and FMS-like tyrosine kinase 3 ligand (FLT3L).

Preferably, the cell population of the present invention is cultured in a serum-free medium.

The cell population of the present invention further expresses CD31 and CXCR4. Moreover, it also expresses CD105.

Examples of mononuclear cells include mononuclear cells derived from peripheral blood, bone marrow or umbilical cord blood.

Preferably, the culturing is carried out under hypoxia conditions. The hypoxia conditions mean conditions that the oxygen concentration is 1-10%.

In an embodiment, the mononuclear cell population is cultured in a medium containing VEGF, bFGF and TPO.

The cell population of the present invention has a revascularization ability. Particularly, the cell population of the present invention has a revascularization ability thorough promotion of neovascular stabilization or maturation.

The present invention provides a cell preparation for revascularization treatment, comprising the cell population of the present invention.

The cell preparation of the present invention has an anti-ischemia and/or vascular maturation effect.

The present invention also provides a diagnostic agent for cancer localization, comprising the cell population of the present invention.

Furthermore, the present invention provides a method of preparing a cell population having a revascularization ability, comprising the steps of:

1) culturing a mononuclear cell population using a medium containing one or more selected from vascular endothelial growth factor (VEGF), basic fibroblast growth factor (bFGF), thrombopoietin (TPO), granulocyte-colony stimulating factor (G-CSF) and FMS-like tyrosine kinase 3 ligand (FLT3L); and 2) collecting a cell population expressing CD11b from cell clusters resulting from the culturing.

In the above method, the medium is preferably a serum-free medium, and the culturing is preferably carried out under hypoxia conditions. In this context, the hypoxia conditions mean conditions that the oxygen concentration is 1-10%.

In an embodiment, the mononuclear cell population is cultured in a medium containing VEGF, bFGF and TPO.

Advantageous Effects of Invention

The cells of the present invention have neovascular stabilization, maturity, and protection functions, promote lumen formation by mature vascular endothelial cells, and functionally normalize tumor vessels. Because the present invention uses monocyte cells as a source, which can be collected from peripheral blood relatively easily, it is useful as an alternative method of conventional revascularization treatments using rare (hematopoietic) stem cells. Moreover, the cells of the present invention have no risk of causing infection because they are obtained by inducing differentiation of monocyte cells under conditions free from animal serum, and can provide a safe cell preparation that can be clinical applied.

BRIEF DESCRIPTION OF DRAWING

The patent or application file contains at least one drawing executed in color. Copies of this patent or patent application publication with color drawing(s) will be provided by the Office upon request and payment of the necessary fee.

FIG. 2-1 shows blood vessel maturation by adherent cells obtained by differentiation-inducing culture of mouse bone marrow mononuclear cells in EGM2-MV medium supplemented with 10% FBS.

FIG. 2-2 shows a transplantation result of adherent cells obtained by differentiation-inducing culture of mouse bone marrow mononuclear cells in EGM2-MV medium supplemented with 10% FBS, to a tumor-bearing nude mouse.

FIG. 15-1 shows the results of differentiation-inducing culture of human peripheral blood mononuclear cells in X-VIVO 15 medium supplemented with 50 ng/mL VEGF, 50 ng/mL bFGF, and 0-100 ng/mL TPO.

FIG. 15-2 shows a quantitative analysis result of cell aggregates obtained by differentiation-inducing culture of human peripheral blood mononuclear cells in X-VIVO 15 medium supplemented with 50 ng/mL VEGF, 50 ng/mL bFGF, and 0-100 ng/mL TPO.

FIG. 19-1 shows the results of 2 color flow cytometry analysis of a CD11b-positive fraction of human peripheral blood mononuclear cells.

FIG. 19-2 shows the results of 2 color flow cytometry analysis of a weakly CD11b-positive fraction (CD11b$^{dim}$) of a cell population obtained by differentiation-inducing culture of human peripheral blood mononuclear cells in X-VIVO 15 medium supplemented with 50 ng/mL VEGF and 50 ng/mL bFGF for four days.

FIG. 19-3 shows the results of 2 color flow cytometry analysis of a strongly CD11b-positive fraction (CD11b$^{bright}$) of a cell population obtained by differentiation-inducing culture of human peripheral blood mononuclear cells in X-VIVO 15 medium supplemented with 50 ng/mL VEGF and 50 ng/mL bFGF for four days.

FIG. 19-4 shows human peripheral blood mononuclear cells and cell population obtained by differentiation-inducing culture of CD11b-positive fraction and CD14-positive fraction thereof in X-VIVO 15 medium supplemented with 50 ng/mL VEGF and 50 ng/mL bFGF.

FIG. 19-5 shows the results of 2 color flow cytometry analysis separating with magnetic beads with labeled antibodies a CD11b-positive fraction of a cell population obtained by differentiation-inducing culture of human peripheral blood mononuclear cells in X-VIVO 15 medium supplemented with 50 ng/mL VEGF and 50 ng/mL bFGF for four days.

FIG. 21-1 shows 2 color flow cytometry analysis results (CD14, UEA-lectin affinity) of peripheral blood mononuclear cells of a multiple myeloma patient and CD11b-positive cells among cells obtained by differentiation-inducing culture in X-VIVO 15 medium supplemented with 50 ng/mL VEGF and 50 ng/mL bFGF.

FIG. 21-2 shows the results of expression analysis of TPO receptor, G-CSF receptor, and CXCR4 in cells obtained by differentiation-inducing culture of CD11b-positive peripheral blood mononuclear cells of a multiple myeloma patient in X-VIVO 15 medium supplemented with 50 ng/mL VEGF and 50 ng/mL bFGF.

FIG. 23-1 shows the results of lower limb ischemia model examination.

FIG. 23-2 shows fluorescent microscope photographs (×20 objective) for the immunohistological detection with an anti-BS1-lectin antibody (nude mouse lower limb ischemia model examination).

FIG. 23-3 shows the results of quantification using ImageJ software, of functional blood vessels visualized with BS1-lectin near ischemic zone (nude mouse lower limb ischemia model examination).

FIG. 25 shows gene expression analysis results by quantitative RT-PCR in CD11b-positive cells derived from peripheral mononuclear cells of a multiple myeloma patient who received G-CSF after chemotherapy. In each graph, from the left, CD11b-positive cells purified with magnetic beads (fre CD11b), cells obtained by culturing in X-VIVO 15 medium supplemented with 50 ng/mL VEGF and 50 ng/mL bFGF in 20% oxygen (cul CD11b in 20% $O_2$), in 5% oxygen (cul CD11b in 20% $O_2$) in X-VIVO 15 medium supplemented with 50 ng/mL VEGF and 50 ng/mL bFGF.

Figure 1:
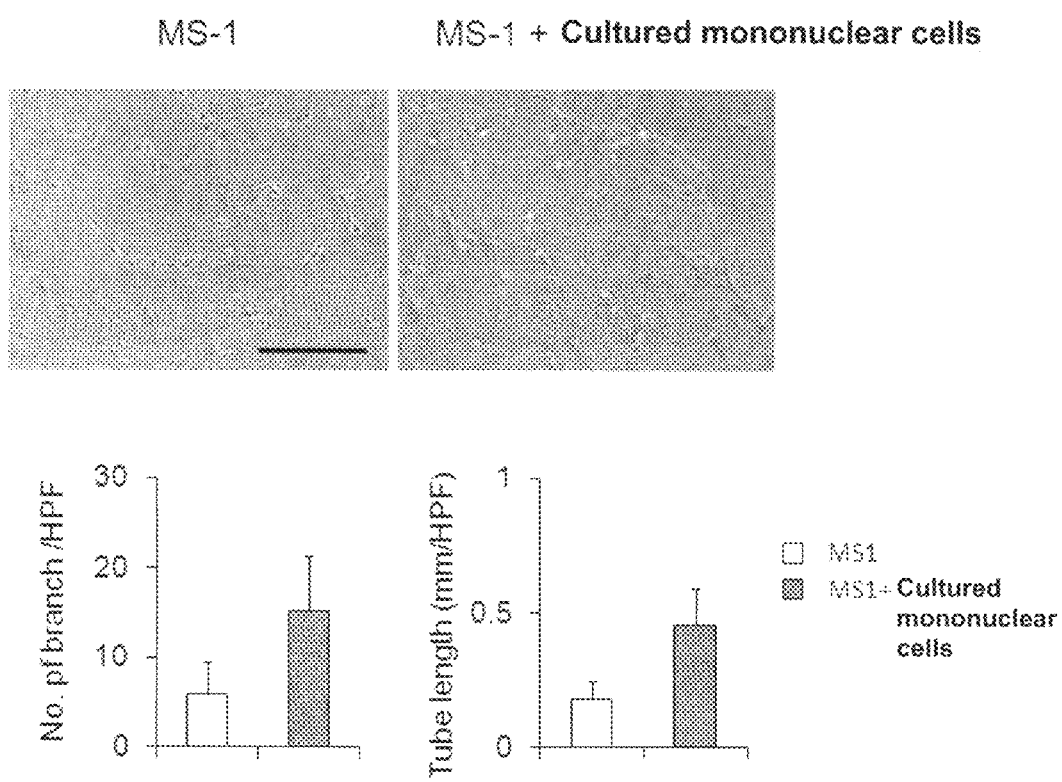
FIG. 1 shows the promotion of lumen formation of MS-1 by adherent cells obtained by differentiation-inducing culture of mouse bone marrow mononuclear cells in EGM2-MV medium supplemented with 10% FBS.

This application claims the priority of Japanese Patent Application No. 2009-93459, and the contents thereof are included herein.

DESCRIPTION OF EMBODIMENTS

1. Cell Population of the Present Invention

The cell population of the present invention is a CD11b-positive cell population having revascularization ability obtained by inducing differentiation of mononuclear cells in mammal.

1.1 Origins

The cell population of the present invention is derived from "mononuclear cells". "Mononuclear cells" are mononuclear mesenchymal cell populations distributed widely in connective tissues, lymphoid tissues, and bloodstream, and classified into migratory mononuclear white blood cells, represented by monocytes and lymphocytes, and mononuclear phagocyte populations represented by macrophages in tissues. The mononuclear cells used in the present invention are preferably mononuclear cells (white blood cells) derived from peripheral blood, bone marrow or umbilical cord blood, which belong to the former. Particularly, mononuclear cells derived from peripheral blood are preferable in that they are present in abundant and easy to obtain.

A cell population (cell preparation) for safe regenerative medicine avoiding the rejection can be prepared by using mononuclear cells autologous to the patient to whom the mononuclear cells are to be administered.

1.2 Induction of Differentiation

The cell population of the present invention is prepared by differentiation-inducing culture of the mononuclear cell population prepared as described above, using a serum free medium containing appropriate "cytokines". The addition of cytokines allows mononuclear cells to grow suitably even in a serum free medium, and induces their differentiation into cells having a desired revascularization ability. Moreover, the prepared cell population (cell preparation) can be used for clinical applications as it is, without the risk of infection etc. because of the use of serum free medium.

Methods of the differentiation induction (preparation) of the cell population of the present invention will be described in details in the next section, "2. Preparation method of the cell population of the present invention".

1.3 Morphology of the Cell Population

The cell population of the present invention is obtained as weakly adhesive, semi-floating (spheroidal) cell aggregations by culture using a serum free medium. This cell population becomes strongly adhesive, spindle shaped adherent cells when reseeded and cultured in the presence of serum (patient's autologous serum).

1.4 Surface Markers

The cell population of the present invention is characterized by expressing CD11b. "CD11b" is one of the hemocyte differentiation antigens mainly expressed in monocytes and lymphocytes. CD11b-positive cells include aberrant neovascular cells found in cancer etc., CD31 antigen-positive vascular endothelial cells, or relatively undifferentiated cells that differentiate into smooth muscle actin (SMA) antigen-positive parietal cells, as well as immunocytes and lymphocytes such as macrophages, dendritic cells, and natural killer cells. The previous reports have suggested the possibility that CD11b expressing cells have an important role in angiogenesis, such as differentiating into cells having an angiogenesis promoting effect (supra.), while they have also showed that these may finally differentiate into vascular endothelial cells, and also these may not.

The cell population of the present invention expresses CD31 and CXCR4, besides CD11b, and further expresses c-Kit slightly. In addition, the expression of CD105 is also found. The inventors found that CD11b-positive cell population obtained by inducing differentiation of mononuclear cells by a particular method using serum free medium have excellent revascularization ability in vivo and in vitro.

In more detail, the cell population of the present invention is considered to be derived from $CD11b^{dim}/CD31^{dim}/CD14^-$ cell population (mainly lymphocytes) or $CD11b^{bright}/CD31^{bright}/CD14^{bright}$ cell population (mainly monocytes). Moreover, there are a population expressing $CD11b^{dim}/CD14^-/CD8^-/CD31^{dim}/CXCR4^+$, and a population expressing $CD11b^{bright}/CD14^+/CD105^+/CXCR4^+$ as surface marker properties after the differentiation induction. Note that "dim" means weak immunostaining and relatively little expression of the marker and that "bright" means strong immunostaining and relatively much expression of the marker.

Simultaneously, the mononuclear cell population and the CD11b-positive cell population included originally in the mononuclear cell population have low revascularization ability in vivo. Moreover, the cell population which has been called EPCs conventionally are differentiated from the CD11b-negative cell population of the mononuclear cell population, and they are clearly different from the cell population of the present invention in that their expression of surface markers is $CD45^-/CD11b^-/CD34^+/CD133^+/Flk-1^+$.

1.5 Revascularization Ability

The cell population of the present invention does not differentiate into vascular endothelial cells directly, but they promote revascularization and lead to recovering from ischemia and tissue repair by promoting neovascular stabilization and maturation. In other words, when systemically locally administered to a body with an ischemic zone such as cancer, they distributed around new blood vessels and promoted vascular stabilization and maturation by enhancing pericyte lining of new blood vessel (microvasculature) endothelium cell.

"Revascularization ability" means a function of promoting or helping mechanisms for forming new blood vessels in tissue, and includes contributions to any of the following stages: angiogenesis in which existing vascular endothelial cells proliferate and migrate to form new blood vessel; collateral circulation formation in which blood vessels in an ischemic zone are remodeled (enlarged), form a conduit for supplying blood flow to new blood vessel; vasculogenesis in which cells derived from bone marrow reach to an ischemic zone via bloodstream and differentiate into blood vessel endothelial or pericyte.

The cells conventionally defined as endothelial progenitor cells (EPCs) are derived from bone marrow, promote angiogenesis with potency to finally differentiate into vascular endothelial cells, and contribute to revascularization treatment. In contrast, the cell population of the present invention does not differentiate into vascular endothelial cells directly, but they contribute to revascularization treatment by promoting neovascular stabilization and maturation.

2. Preparation Method of Cells

The cell population of the present invention is prepared from mononuclear cell population by the following steps:

1) culturing mononuclear cell population in a serum-free medium containing one or more selected from vascular endothelial growth factor (VEGF), basic fibroblast growth factor (bFGF), thrombopoietin (TPO), granulocyte-colony stimulating factor (G-CSF) and FMS-like tyrosine kinase 3 ligand (FLT3L); and 2) collecting cell population expressing CD11b from cell aggregations.

2.1 Preparation of Mononuclear Cells

Mononuclear cells can be easily separated from each tissue using a commercial kit by a well-known method, for example, by diluting the collected blood appropriately, transferring it into a centrifugation tube containing separation liquid placed in the tube beforehand, centrifuging it at approximately 1500 rpm to separate by the difference of specific gravities. Peripheral blood mononuclear cells comprising lymphocytes and monocytes are collected as a white belt layer between plasma (with yellowish color) and separation liquid (transparent).

2.2 Medium-Serum Free Medium

A medium used in the present invention is particularly not limited, as long as the medium is suitable for culturing mononuclear cells. Standard media include MEM, BME, DME, α-MEM, IMEM, ES, DM-160, Fisher, F12, WE, RPMI, StemSpan, StemPro media and mixtures thereof. Also included are commercial media for lymphocyte culture: for example, GT-T medium (Takara Bio), AIM V medium (Invitrogen), culture medium for T lymphocyte culture (Cosmo Bio), X-VIVO medium (from Lonza); and commercial media for vascular endothelial cells: for example, EGM-2 and EBM-2 media.

Preferably, the above mentioned medium is a "serum free medium", which does not contain animal serum, particularly FBS, FCS, etc. A "serum free medium" is particularly not limited, as long as it is a medium suitable for culture of mononuclear cells; a commercial serum free medium may be used, or a medium may be prepared if necessary. The present inventors established a simple method for inducing differentiation into the cell population of the present invention using a "serum free medium". A serum free medium, which does not contain animal serum, is free from risk of infection etc., and the prepared cell population (cell preparation) can be used for clinical applications as it is.

2.3 Cytokines

"Inducing differentiation" of a mononuclear cell population is carried out by the addition of appropriate "cytokines" to the above serum free medium, and culture. Cytokines allows mononuclear cells to grow suitably even in a serum free medium, and induces their differentiation into cells having a desired revascularization ability.

"Cytokines" used by the present invention include, but are not limited to, vascular endothelial growth factor (VEGF), basic fibroblast growth factor (bFGF), thrombopoietin (TPO), granulocyte-colony stimulating factor (G-CSF), FMS-like tyrosine kinase 3 ligand (FLT3L), Macrophage-colony stimulating factor (M-CSF), hedgehog ligand, CEACAM (carcinoembryonic antigen-related cell adhesion factor) as long as suited to the purpose and the effects of the present invention.

"Vascular endothelial growth factor (VEGF)" is a group of glycoprotein participating in vasculogenesis and angiogenesis. VEGF binds to VEGF receptor (VEGFR) locating mainly on the vascular endothelial cell surface, stimulates cell division, migration, or differentiation, and enhance the microvascular permeability, as well as participate in the activation of monocytes and macrophages. It participates in angiogenesis in a normal body, and also in a process of malignant transformation including vasculogenesis and metastasis of tumor.

Growth factors involved in vasculogenesis, angiogenesis, and lymphangiogenesis include seven of VEGF-A, VEGF-B, VEGF-C, VEGF-D, VEGF-D, VEGF-E, PlGF-1, and PlGF-2. These are collectively called "VEGF family", and occasionally, VEGF may refer to only VEGF-A. Furthermore, some VEGF family members have some subfamilies as well. "Vascular endothelial growth factor (VEGF)" used herein include these VEGF families and subfamilies thereof, as long as it does not impair the purpose and the effects of the present invention.

"Basic fibroblast growth factor (bFGF)" is a heparin-binding division promoting protein, and as a potent angiogenetic factor (peptide), has functions of promoting angiogenesis and arteriogenesis, and participates in the formation of nerves and bones. It is known to have effects of increasing the proliferation of various types of cells in serum free culture or under culture conditions with a little amount of serum.

"Thrombopoietin (TPO)" is a hematopoietic factor participating in the proliferation and differentiation of platelet precursor cells. Platelets differentiate from hematopoietic stem cells via megakaryocytes, and play an important role in blood coagulation and participate in various immunoreactions. TPO is reported as a factor having activity to promote the formation of platelets, and cloned in 1994 for the first time. Later, TPO was found to be a ligand of c-mpl with a function to suppress the formation of megakaryocyte colonies, and it is considered to be a factor important for the production of haemopoietic system cells.

"Granulocyte-colony stimulating factor (G-CSF) is able to promote the production of granulocytes and to enhance functions of neutrophiles. It is secreted mainly from macrophages, and through the action of GM-CSF, targets precursor cells in which differentiation is more directed to granulocytes. Therefore, genetically-modified human G-CSF preparations are used for neutropenia due to cancer chemotherapy and neutropenia associated with aplastic anemia.

"FMS-like tyrosine kinase 3 ligand" (FLT3L) is a tyrosine kinase 3 ligand, and known to regulate the proliferation and differentiation of precursor cells and stem cells in the haemopoietic system via signal transduction through the Flt3 receptor (CD135), one of the receptor-type tyrosine kinases. The Flt3 ligand is known to have a proliferation activity to cells of the monocyte linage such as CD34 or CD133-positive hematopoietic stem cells or dendritic cells, and capable of amplifying these in vivo and in vitro.

Cytokines used in the present invention, such as VEGF, bFGF, TPO, FLT3L etc. may be naturally occurring or recombinant. Preferably, these cytokines are from the same species as the mononuclear cells to be used. Therefore, human VEGF is preferable when using human mononuclear cells. VEGF to be used may be a commercial product (a reagent or pharmaceutical product), or recombinantly produced based on known sequence information.

The present invention uses a serum free medium containing at least one of the cytokines mentioned above. Preferably, the serum free medium contains VEGF, bFGF and TPO. Because the expression of TPO receptor is low in CD11b-positive cells, the possibility of working via a paracrine effect through CD11b-negative cells is expected. And because, in the case of young CD11b-positive cells derived from bone marrow with G-CSF, elevating expression of the TPO receptor is seen in the process of inducing differentiation, a direct effect is expected, the action mechanisms remain unclear.

Although the amount of a cytokine to be added to the medium is determined appropriately depending on cells to be used, it is in the range of 1-100 µg/ml in general.

2.4 Culture Conditions

Culture is carried out in the conditions that are usually used for culture of lymphocyte using surface-treated culture dishes. In other words, they are 37° C. in temperature and 20% of oxygen concentration.

Preferably, culture is carried out under a hypoxia conditions. Here, "hypoxia conditions" mean the conditions that oxygen concentration is at least less than atmospheric oxygen content (approximately 21%), and specifically means to be 1%-10% of oxygen concentrations. Culturing under hypoxia conditions lead to the improvement of cellular survival rate, and acquisition of cells with a desired revascularization ability in high efficiencies.

Preferably, culture of cells is carried out in the cell preparation facility of the GMP standard, "CPC" (Cell Processing Center). Preferably, the preparation of "cells of clinical grade" for the administration to a subject is carried out in a facility specially designed for sterile operation of cells, more specifically, CPC in which cleanliness is secured by air conditioning control, room pressure control, temperature-humidity control, particle counter, HEPA filter, etc. Moreover, it is preferred that not only CPC facility itself but also all equipment to be used in CPC are guaranteed for their performance by validation, and their functions are monitored and recorded at any time. It is desirable that all cell processing operations in CPC is strictly managed and recorded according to "Standard Operating Procedure".

2.5 Separation of CD11b-Positive Cells

By culture using a serum free medium, the cells are obtained as weakly adhesive, semi-floating (spheroidal) cell aggregations. From these cell aggregations, CD11b-expressing cells are collected. The collection of CD11b-expressing cells can be carried out easily using CD11b antibody according to conventional procedures. For example, CD11b-positive cells may be separated using such as CD11b antibody-labeled magnetic beads, the separation with a cell sorter using a fluorescence-labeled CD11b antibody, or using a column in which a CD11b antibody is immobilized. The CD11b antibody may be a commercial product, or may be prepared using CD11b or a partial peptide thereof according to conventional procedures.

3. Cell Preparation 3.1 Cell Preparation for Revascularization Treatment

The cell population of the present invention does not differentiate into vascular endothelial cells directly, but it promotes revascularization by promoting neovascular stabilization and maturation and lead to recovery from ischemia or tissue repair.

Therefore, the cell population of the present invention can be used as "cell preparation for revascularization treatment" which promotes blood vessel stabilization and maturation when administered to a patient with an ischemic zone such as cancer. The cell preparation of the present invention is clearly different from conventional cell preparation for revascularization treatment using EPC in that itself does not differentiate into vascular endothelial cells directly, but exerts the revascularization ability through the promotion of neovascular stabilization or maturation.

The administration method of the cell preparation of the present invention is particularly not limited, but depending on the site of application, local transplantation by surgical means, intravenous administration, lumber puncture administration, local infusion administration, subcutaneous administration, intradermal administration, intraperitoneal administration, intramuscular administration, intracerebral administration, intracerebroventricular administration or intravenous administration, or the like are considered. Particularly, a local administration or transvenous administration is preferred as administration method to ischemic site including cancer.

It is known that in abnormal new blood vessels seen in cancer or the like, the expression of a receptor for an angiogenic factor, such as VE-cadherin, VEGF receptor 1 (VEGFR1), SDF-1 receptor (CXCR4), and angiopoietin-1 receptor (Tie-2), together with CD11b antigen is found (supra). The cell population of the present invention has selective tropism to tumor tissue and ischemic zones, and it is possible that, when administered locally or transvenously, it may localize to tumor, and restore the blood vessel structures and functions in tumor blood vessels.

The angiogenesis ability of mononuclear cells obtained from peripheral blood of patients having a lifestyle-related disease, such as hypertension, diabetes, and hyperlipidemia, or elderly patients may be impaired. In patients with such various complications, preparing the cell preparation of the present invention using mononuclear cells obtained from their peripheral blood enables the reproduction treatment using autologous cells.

The cell preparation of the present invention may contain a scaffold material or component assisting the maintenance or proliferation of cells, or the administration to an affected part, or another pharmaceutically acceptable carrier.

Components necessary for maintenance or proliferation of cells include carbon sources, nitrogen sources, vitamins, minerals, salts, medium ingredients such as various cytokines, or extracellular matrix preparations such as Matrigel™.

Scaffold materials and components assisting the administration to an affected part include: biodegradable polymers, for example, collagen, polylactic acid, hyaluronic acid, cellulose and these derivatives and complexes of two or more thereof; aqueous solution for injection, for example, physiological buffer solution, such as saline, media and PBS, isotonic solutions containing glucose or another adjuvant (e.g., D-sorbitol, D-mannose, D-mannitol, sodium chloride) etc.; and may be used with a suitable solubilizing agent, for example, alcohol, specifically, ethanol, polyalcohol, for example, propylene glycol, polyethylene glycol, non-ionic surfactant, for example, polysorbate 80, HCO-50, etc.

In addition, depending on need, the preparation may contain a pharmaceutically acceptable organic solvent, Polyvinyl alcohol, polyvinylpyrrolidone, carboxy vinyl polymer, sodium carboxymethylcellulose, sodium polyacrylate, sodium alginate, water-soluble dextran, carboxymethyl starch sodium, pectin, methylcellulose, ethyl cellulose, xanthan gum, Arabian gum, casein, agar, polyethylene glycol, diglycerine, glycerin, propylene glycol, vaseline, paraffin, stearyl alcohol, stearic acid, mannitol, sorbitol, lactose, a surfactant acceptable as a pharmaceutical additive, buffer, emulsifier, suspender, soothing agent, stabilizer, etc.

Actual additives are selected from those mentioned above, alone or in appropriate combination, depending on the dosage form of the therapeutic agent of the present invention, but they are not limited to these. For example, when used as a preparation for injection, a purified antibody may be dissolved in a solvent, e.g., saline, buffer, glucose solution; and used as those to which an adsorption inhibitor, e.g., Tween80, Tween20, gelatin is added.

Diseases that can be treated with the cell preparation of the invention include any diseases needing revascularization: for example, wounds including bedsore/skin ulcer, surgical scar, and refractory peptic ulcer; inflammatory diseases including chronic inflammatory enteropathies such as ulcerative colitis and Crohn disease; severe limbs ischemia; ischemic heart disease including myocardial infarction, angina, and heart failure; cerebral infarction; diabetic neuropathy; cancer associated with severe ischemia etc. Particularly, diseases that are difficult to treat with conventional medicine, such as chronic critical limb ischemia (occlusive arteriosclerosis, Buerger's disease), refractory ischemic heart disease, cancer associated with severe ischemia, and diabetic vascular disorder including retinopathy are preferred to be treated with the preparation.

3.2 Diagnostic Agent for Cancer Localization

The cell population of the present invention has selective tropism to tumor tissue and ischemic zones. Therefore, by labeling the cell population of the present invention with nanoparticles etc., it can be applied to imaging diagnosis to localize cancer with ischemia or metastatic foci. Labeling of cells can be performed easily, according to conventional procedures, by labeling them with a magnetic substance or a fluorescent dye.

3.3 Other

Because the cell population of the present invention has selective tropism to tumor tissue, it may be possible to use it as a carrier of an anticancer agent or a protein or agent with cytotoxicity to tumor cells.

EXAMPLES

Hereinafter, the present invention is specifically explained according to the examples, but it is not to be restricted to these examples.

Example 1

Induction of Differentiation of Mouse Mononuclear Cells in EGM2-MV Medium

From mouse bone marrow, the mononuclear cells were prepared as follows. Mouse thighbone etc. were crushed by using a mortar and DPBSE (PBS containing EDTA at the concentration of 5 mM), and bone marrow fluid was collected. The collected bone marrow fluid was filtrated using a membrane filter of 70 μm diameter to collect bone marrow cell suspension. The cells were suspended in 10 ml of DPBSE. This suspension was gently overlayed on 4 ml of Histopaque 1083 (Sigma) in a 15 ml centrifugal tube. After separating this mixture by density gradient centrifugation (400 g at room temperature for 20 minutes), cells layered in the middle were collected with pipette to isolate bone marrow mononuclear cells (BM-MNC).

The obtained mouse bone marrow mononuclear cells were cultured with inducing differentiation for one week in EGM2-MV medium supplemented with 10% FBS in a temperature sensitive culture dish treated with rat vitronectin (UpCell; CellSeed; http://www.cellseed.com/product/004.html) to obtain adherent cells.

EGM2-MV medium: containing EGF, VEGF, IGF, and bFGF (The concentrations of growth factors are not in public; Lonza).

Culture condition: culturing in 20% oxygen and 5% $CO^2$ and at 37° C. for four days to allow adherent cells to float at the room temperature; reseeding in a new UpCell culture dish not treated for coating; and allowing adherent cells to float again after three days and collecting them.

The effect of the adherent cell population differentiated from mouse bone marrow mononuclear cells on vasculogenesis was examined.

(1)

The adherent cells obtained in the preceding paragraph were labeled with GFP, co-cultured on Matrigel with low contents of growth factors in a medium similar to those for mouse vascular endothelial cell line MS-1. As a result, it was confirmed that the lumen formation of MS-1 was enhanced by adding cultured mononuclear cells (FIG. 1).

(2)

$10^5$ adherent cells obtained in the preceding paragraph were hypodermically transplanted three times in total at intervals of four days, into a nude mouse that was received transvenous transplantation of human pancreatic carcinoma cell line KP-1N. Thus, when the tumor diameter reached 8 mm or more, $5 \times 10^5$ of cultured mononuclear cells were transvenously transplanted, tumor tissue was collected after one week, tumor blood vessels were analyzed immunohistologically.

Figures 1, 15:
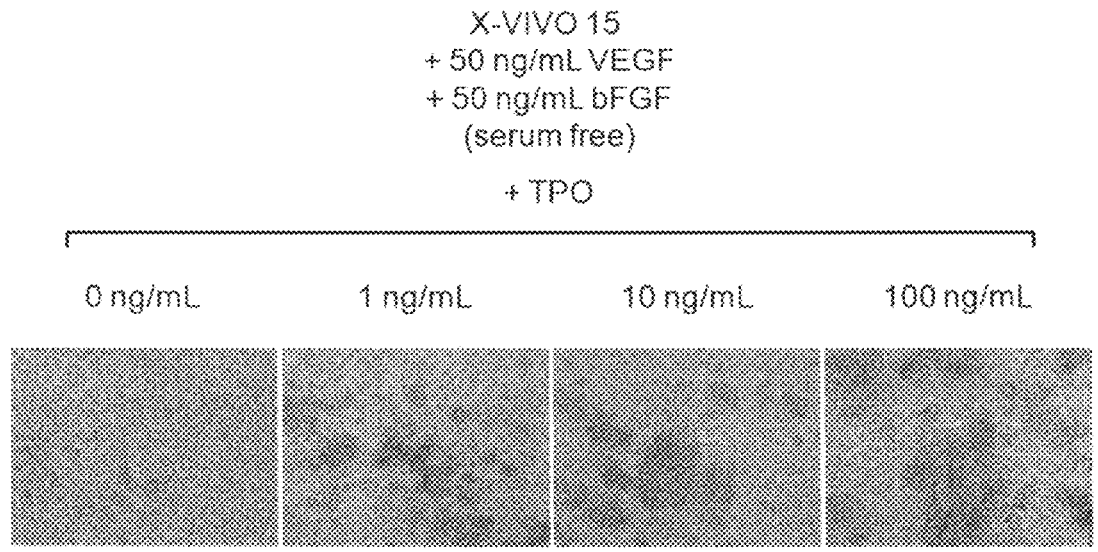
Figures 2, 15:
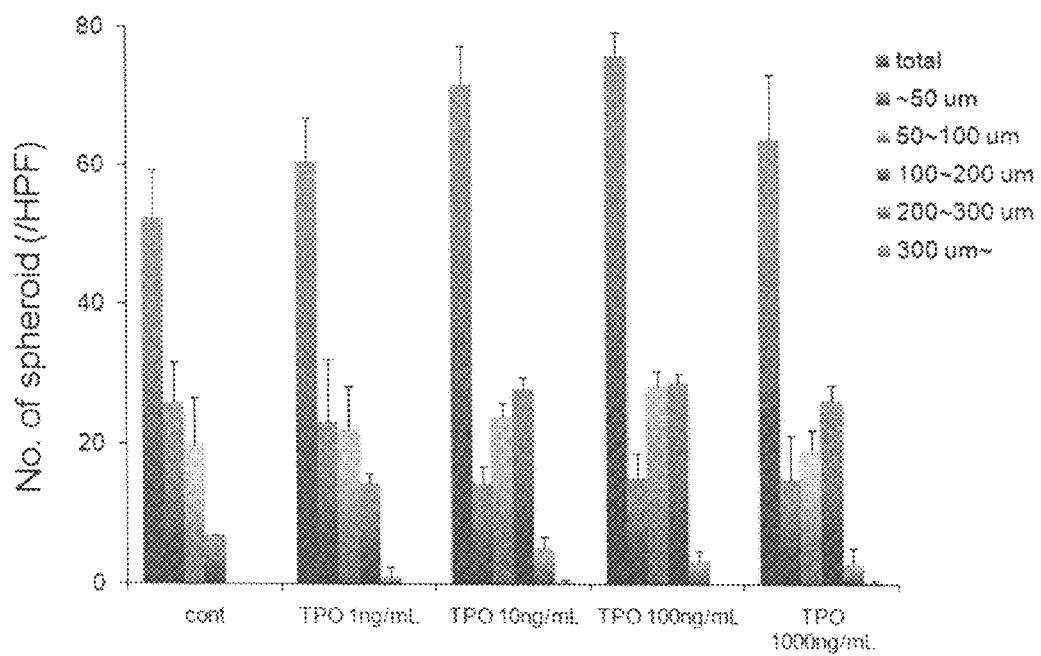

CD31 antibody (Vascular endothelial cell; red, BD), NG2 antibody (pericyte; green, Millipore), and nuclear staining (blue) were carried out, and the luminal area and the ratio of mature blood vessels with pericyte support, to microvessels were calculated. The result confirmed that transplantation of cultured mononuclear cells improve the vessel area of tumor blood vessels and support by NG2-positive pericytes (blood vessel maturation; FIG. 2-1).

(3)

Moreover, CD31 antibody (vascular endothelial cells; red), and nuclear staining (blue) were carried out, and the localization of transplanted mononuclear cells was examined with fluorescence labeling with GFP (green). The result confirmed that transplanted cells distribute only perivascular area of tumor blood vessels and does not differentiate into vascular endothelial cells (FIG. 2-2).

(4)

Figure 3:
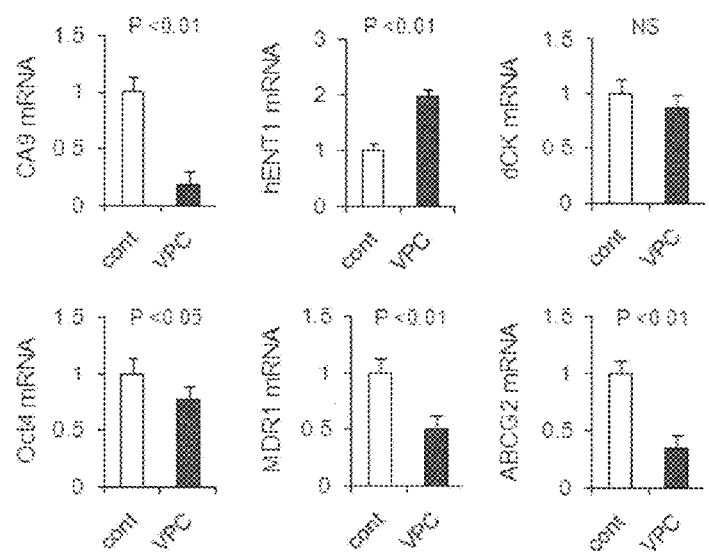
FIG. 3 shows gene expression analysis results by quantitative RT-PCR using the TaqMan probe (top left: CA9, top center: hENT1, top right: dCK, bottom left: Oct4, bottom center: MDR1, bottom right: ABCG2).

RNA was extracted from the tumor obtained by above (2), and the gene expression of cancer cell origin (human pancreatic carcinoma cell KP-1N) was analyzed by quantitative RT-PCR using TaqMan probe (FIG. 3). The result confirmed that the expression of CA9 decreases remarkably, while the expression of hENT increases, the expression of the stem cell marker Oct4, MDR-1 that relates to the drug resistance, and ABCG2 etc. decreases.

Discussion:

The foregoing results confirmed that adherent cells obtained by inducing the differentiation of mononuclear cells using EGM2-MV medium supplemented with serum can enhance the stabilization of new blood vessels, and repair the structural aberration of tumor blood vessels.

Significant decrease of expression of CA9 in quantitative RT-PCR suggested that structural stabilization of tumor blood vessels associated with the transplantation of the mouse bone marrow cells cultured by the above method (differentiation-inducing culturing in EGM2-MV medium supplemented with 10% FBS) leads to recovering from the hypoxia environment in cancer tissue. Moreover, increase in the expression of hENT suggested that uptake of gemcitabine hydrochloride, which is a standard therapeutic agent for pancreas cancer, improves. Further, the decrease in the expression of stem cell marker suggested that transplantation of the cultured mouse bone marrow cells decreases the cancer stem cell fraction, and reduces the resistance to cancer treatments.

Example 2

Induction of Differentiation of CD11b Positive-Fraction of Mouse Mononuclear Cells Mononuclear cells were prepared from mouse bone marrow similar to Example 1. Next, a CD11b-positive fraction is prepared from the obtained mouse bone marrow mononuclear cells using immunomagnetic beads (Miltenyi Biotec.) on which a CD11b antibody is immobilized.

(1)

Figure 4:
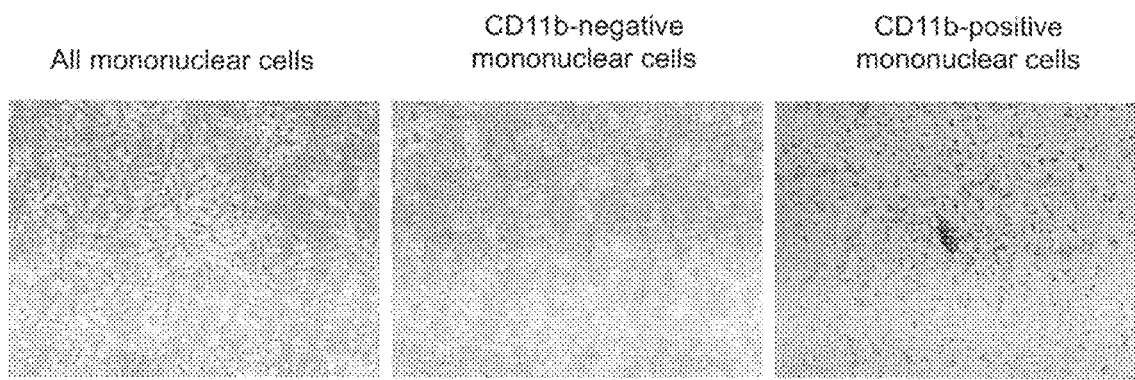
FIG. 4 shows morphology of CD11b-positive and negative fractions of mouse bone marrow mononuclear cells.

Among cells in the CD11b-positive fraction, adherent cells in spindle shape similar to all mononuclear cells were observed. On the other hand, cells in similar shape were scarce when the CD11b-negative fraction was used (FIG. 4). From this, cells in spindle shape seen in the early stage of culturing are considered to be of monocyte origin.

(2)

When cells in the CD11b-positive fraction were cultured for three weeks in EGM2-MV medium supplemented with 10% FBS in a culture dish treated with rat vitronectin, the expansion and enlargement of cells were seen, but the cells showed no tendency of proliferation. Thus, CD11b-positive cells are observed as adherent cells in spindle shape from the early stage of culturing, show weak colony formation, and have poor proliferation potency (FIG. 5, upper row).

Figure 5:
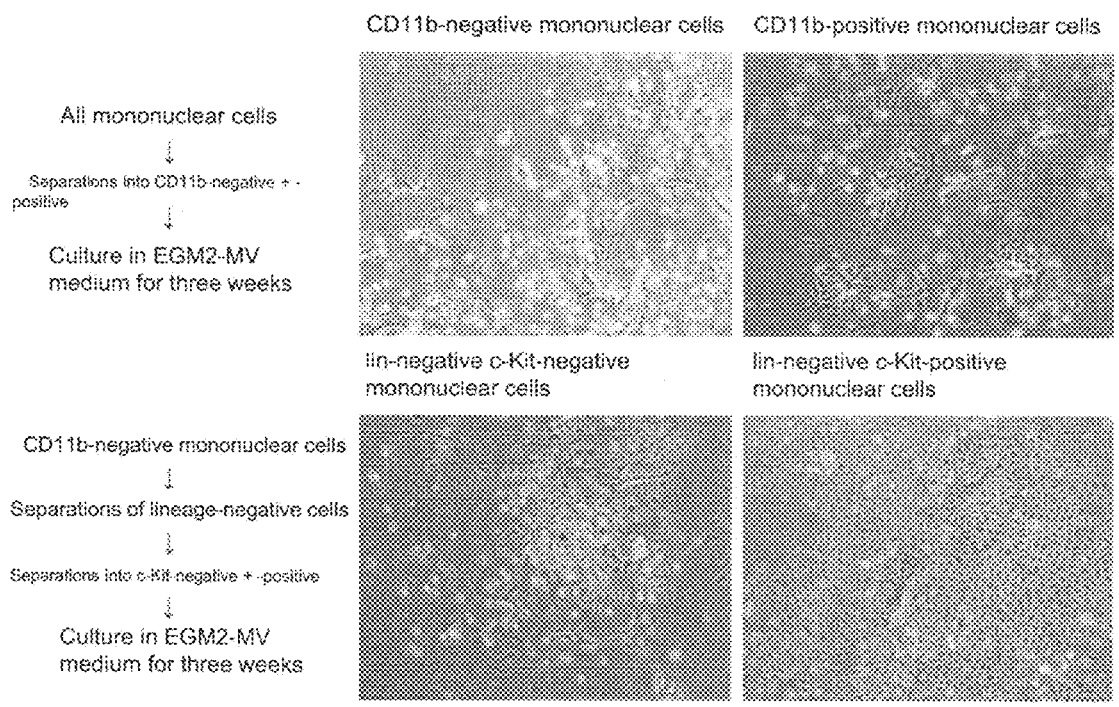
FIG. 5 shows the results of differentiation-inducing culture of a CD11b-positive fraction of mouse bone marrow mononuclear cells in EGM2-MV medium supplemented with 10% FBS.

On the other hand, when differentiation-inducing cultured, particularly, Lineage-negative, c-Kit-positive fraction (fraction containing hematopoietic stem cells) in CD11b-negative fraction for three weeks or more in EGM2-MV medium supplemented with 10% FBS as well, they proliferated starting with colony formation, in which the appearance of cells in flagstone shape was observed (FIG. 5). Because these cells can be successively cultured, they appeared to be close to EPC with proliferation potency, it seemed that they differed from the cells derived from CD11b-positive cells (FIG. 5, bottom row).

Discussion:

From the foregoing results, the cells that have been called vascular endothelial progenitor cells (EPC) conventionally appeared to be derived from particularly Lineage-negative, c-Kit-positive fraction in CD11b-negative fraction, and, on the other hand, many of early adherent cells seemed CD11b expressing cells.

Example 3

Induction of Differentiation of Human Mononuclear Cells Under Various Conditions 20 mL of DPBSE was added to 30 mL of peripheral blood obtained from a healthy volunteer. Baffy court was collected by spinning it at 400×g, 20° C., for 35 minutes. It was resuspended into 20 mL of DPBSE, then separated by density gradient centrifugation (400 g at room temperature for 20 minutes) using Histopaque 1077 (Sigma). Mononuclear cells were isolated by collecting cells layered in the middle with pipette, and cultured in EBM-2 supplemented with EGM2-MV medium kit for microvascular endothelial cell medium (Lonza) on a plate coated with human fibronectin for 4-0.7 days to obtain adherent cells.

(1)

Figure 6:
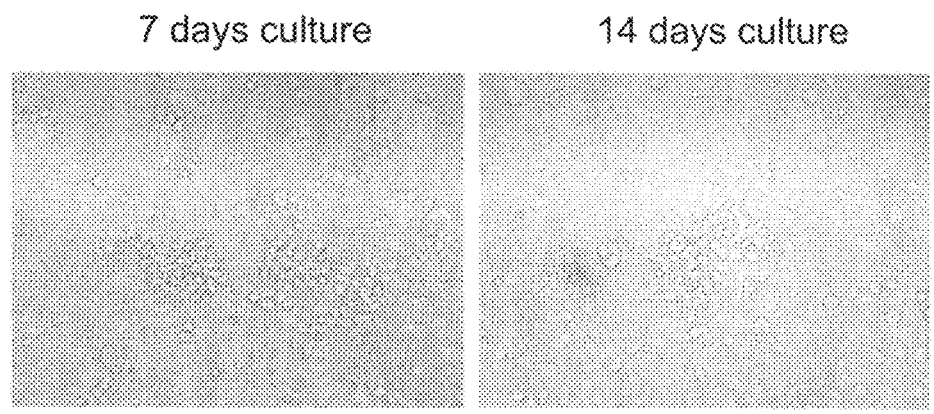
FIG. 6 shows the results of differentiation-inducing culture of human peripheral blood mononuclear cells in EGM2-MV medium supplemented with 10% FBS.

Human peripheral blood mononuclear cells were cultured with inducing differentiation in EGM2-MV medium supplemented with 10% FBS in culture dish treated with human fibronectin. It was confirmed that cells keep round-to-spindle shape well for about one week of culture period, when cultured for about two weeks, cells show symptom of senility such as expansion and enlargement, and reduces the viability significantly (FIG. 6). The composition of EGM2-MV medium and culture conditions are same as Example 1.

(2)

Figure 7:
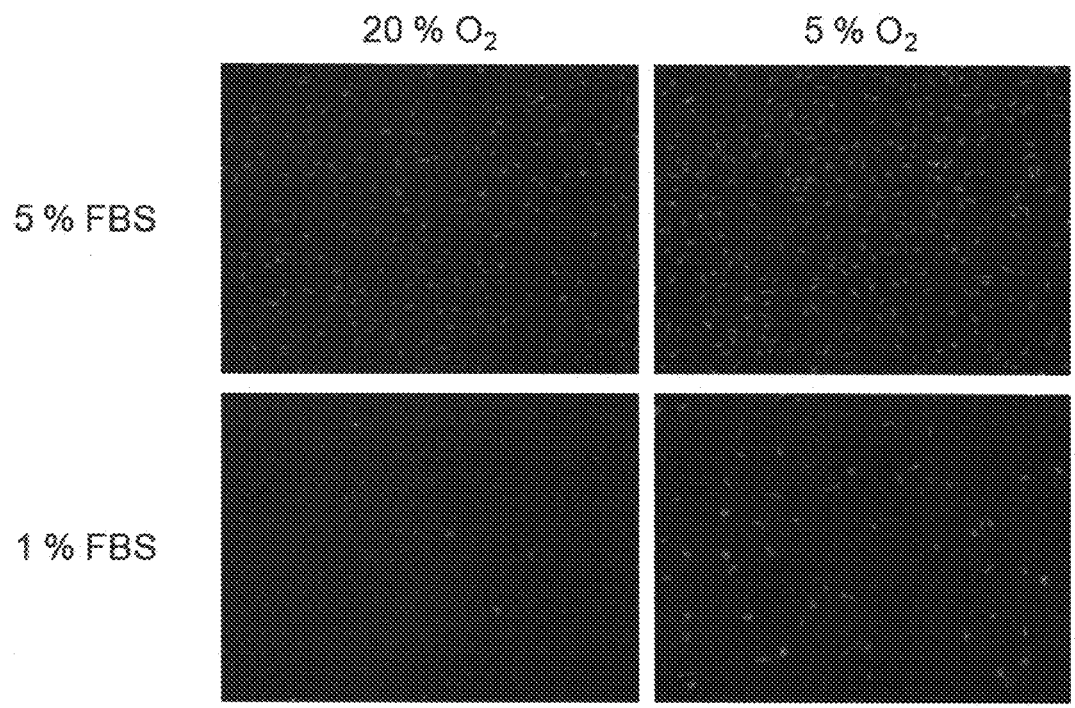
FIG. 7 shows the results of differentiation-inducing culture of human peripheral blood mononuclear cells in EGM2-MV medium supplemented with 5% or 1% FBS in a hypoxia environment.

DiI-acLDL labeled with acetylated LDL was added to EGM2-MV medium supplemented with 5% or 1% FBS. Similar to the preceding paragraph, human peripheral blood mononuclear cells were cultured with inducing differentiation in a culture dish treated with human fibronectin. It was confirmed that culturing adherent cells visualized by uptaking acetylated LDL, under a hypoxia environment with 5% oxygen reduces symptoms of senility such as expansion and enlargement, improves the cell viability, and decreases serum dependency (FIG. 7).

(3)

Figure 8:
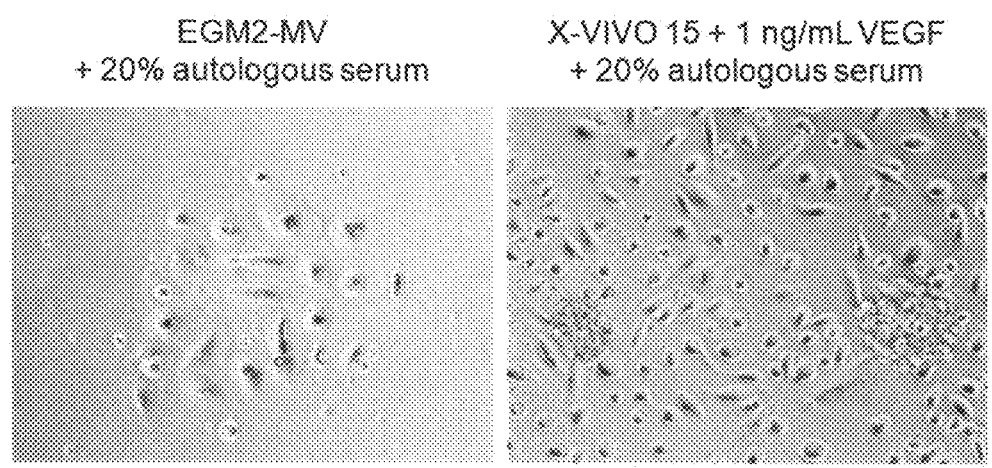
FIG. 8 shows the results of differentiation-inducing culture of human peripheral blood mononuclear cell in X-VIVO 15 medium supplemented with 20% autologous serum (also supplemented with 1 ng/mL human VEGF) and EGM2-MV medium supplemented with 20% autologous serum.

Human peripheral blood mononuclear cells were cultured with inducing differentiation in X-VIVO 15 medium supplemented with 20% autologous serum (also with 1 ng/mL human VEGF) in culture dish treated with human fibronectin. X-VIVO 15 medium is suitable for culture of purified CD3+ lymphocyte separated from peripheral blood and human tumor, as well as human monocyte, macrophage, various cell line, granular leukocyte, and natural killer (NK) cells. Culture was carried out in 20% oxygen and 5% $CO_2$ and at 37° C. It was confirmed that compared with cells obtained in EGM2-MV medium supplemented with 20% autologous serum, the obtained adherent cells show suppressed levels of symptoms of cellular senility observed two weeks after the start of culturing (FIG. 8).

(4)

Figure 9:
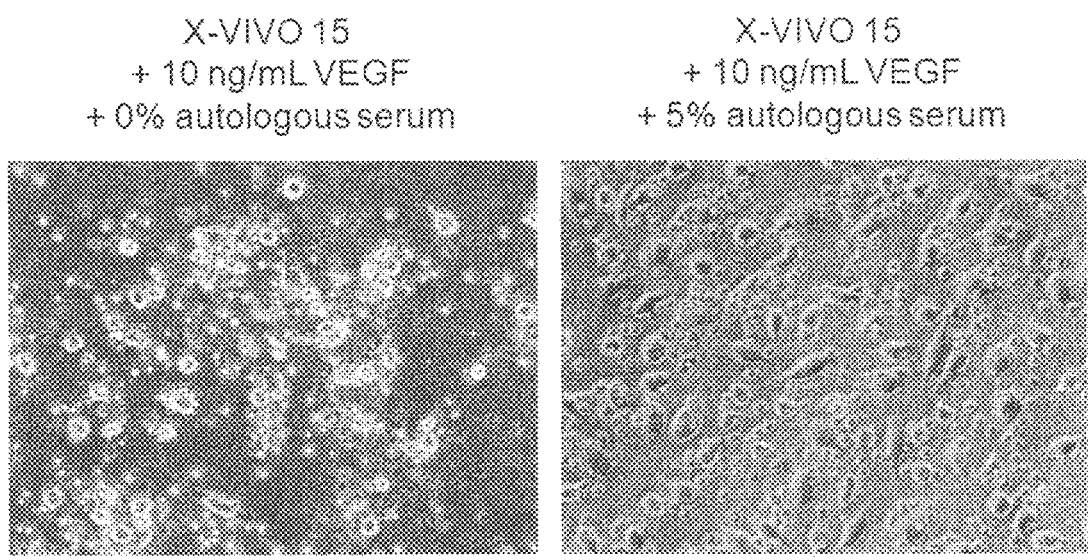
FIG. 9 shows the results of differentiation-inducing culture of human peripheral blood mononuclear cells in X-VIVO 15 medium supplemented with 5% autologous serum, 50 ng/mL VEGF, and 50 ng/mL bFGF.

Similar to the preceding paragraph, human peripheral blood mononuclear cells was cultured with inducing differentiation for seven days in X-VIVO 15 medium supplemented with 5% autologous serum, 10 ng/mL VEGF and 10 ng/mL basic fibroblast growth factor (bFGF) in culture dish treated with human fibronectin. The obtained adherent cells showed spindle shapes (FIG. 9).

(5)

Figure 10:
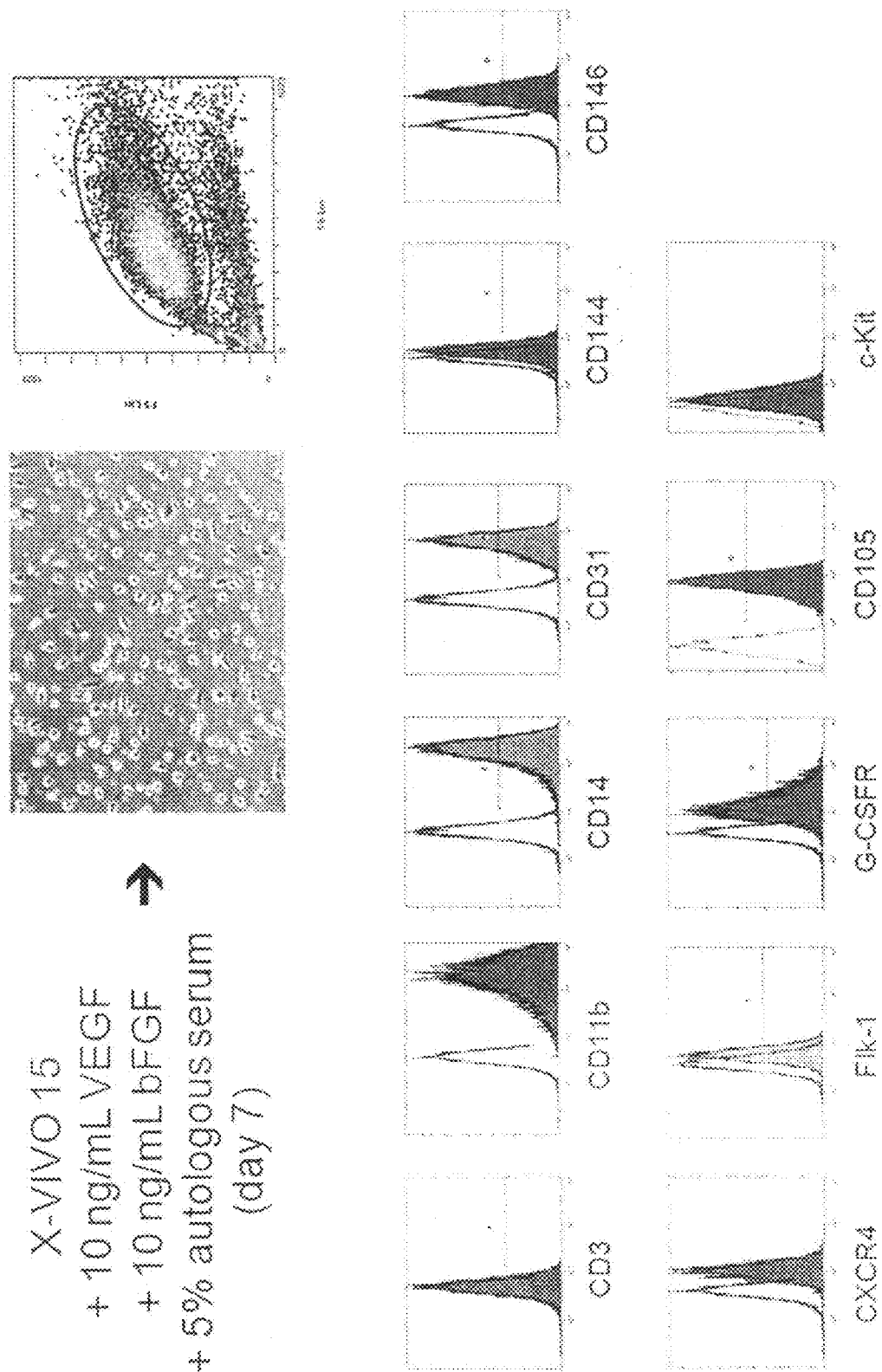
FIG. 10 shows expression of surface markers on adherent cells obtained by differentiation-inducing culture of human peripheral blood mononuclear cells in X-VIVO 15 medium supplemented with 5% autologous serum, 50 ng/mL VEGF, and 50 ng/mL bFGF.

Similar to the preceding paragraph, human peripheral blood mononuclear cells was cultured with inducing differentiation for seven days in X-VIVO 15 medium supplemented with 5% autologous serum, 10 ng/mL VEGF and 10 ng/mL bFGF in culture dish treated with human fibronectin. Expression of surface markers on the obtained adherent cells was confirmed by using flowcytometry. The results confirmed that the adherent cells express CD11b, CD14, CD31, CD105, CD146, VEGF receptor 2 (VEGFR2), SDF-1 receptor (CXCR4), and the G-CSF receptor on the cell membrane (FIG. 10).

(6)

Figure 11:
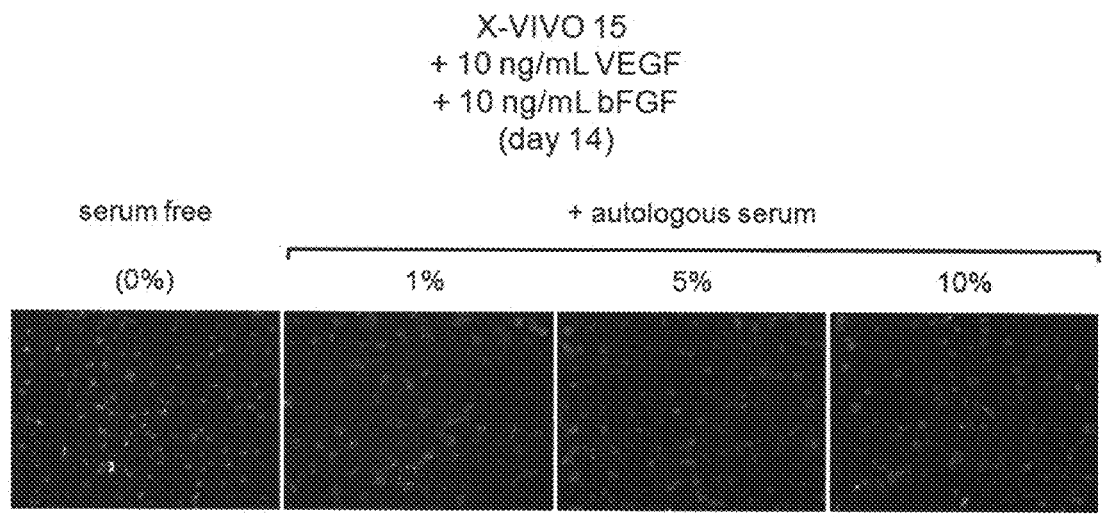
FIG. 11 shows the results of differentiation-inducing culture of human peripheral blood mononuclear cells in X-VIVO 15 medium supplemented with 50 ng/mL VEGF and 50 ng/mL bFGF in the presence of 0, 1, 5, 10% autologous serum.

DiI-acLDL labeled with acetylated LDL was added to X-VIVO 15 medium supplemented with 0, 1, 5, and 10% autologous serum, 10 ng/mL VEGF and 10 ng/mL bFGF, and human peripheral blood mononuclear cells were cultured with inducing differentiation in a culture dish treated with poly-L-lysine (PLL) for 14 days. The results confirmed that weakly adherent living cells visualized by uptaking acetylated LDL labeled with DiI are present even under serum free conditions (FIG. 11).

(7)

Figure 12:
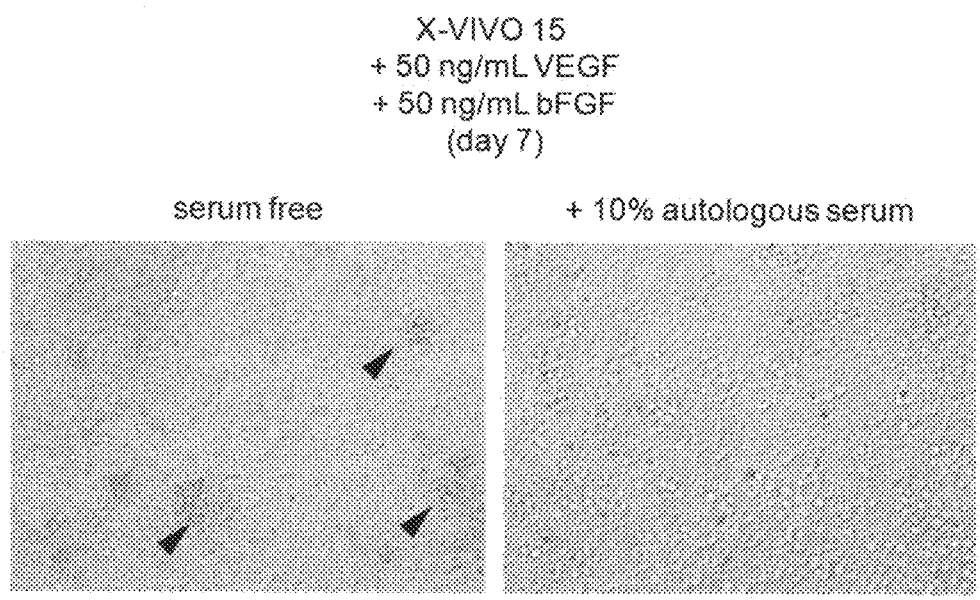
FIG. 12 shows the results of differentiation-inducing culture of human peripheral blood mononuclear cells in X-VIVO 15 medium supplemented with 50 ng/mL VEGF, 50 ng/mL bFGF in the presence or absence of 10% autologous serum.

Human peripheral blood mononuclear cells were cultured with inducing differentiation for one week in X-VIVO 15 medium supplemented with 50 ng/mL VEGF and 50 ng/mL bFGF in a culture dish. The results confirmed that semifloating (spheroidal) cell aggregates appear in serum free conditions. It was confirmed that these cell aggregates show weak cell adhesion, while in the presence of 10% autologous serum, aggregates of cells in round-to-spindle shape appear, in which cells show enhanced adhesion and increased cell area (FIG. 12). The adherent cells seen in these serum-containing medium does not seem to be EPCs because they are CD11b-positive and express the monocyte lineage markers such as CD14, although they have uptaking ability of acLDL.

(8)

Figure 13:
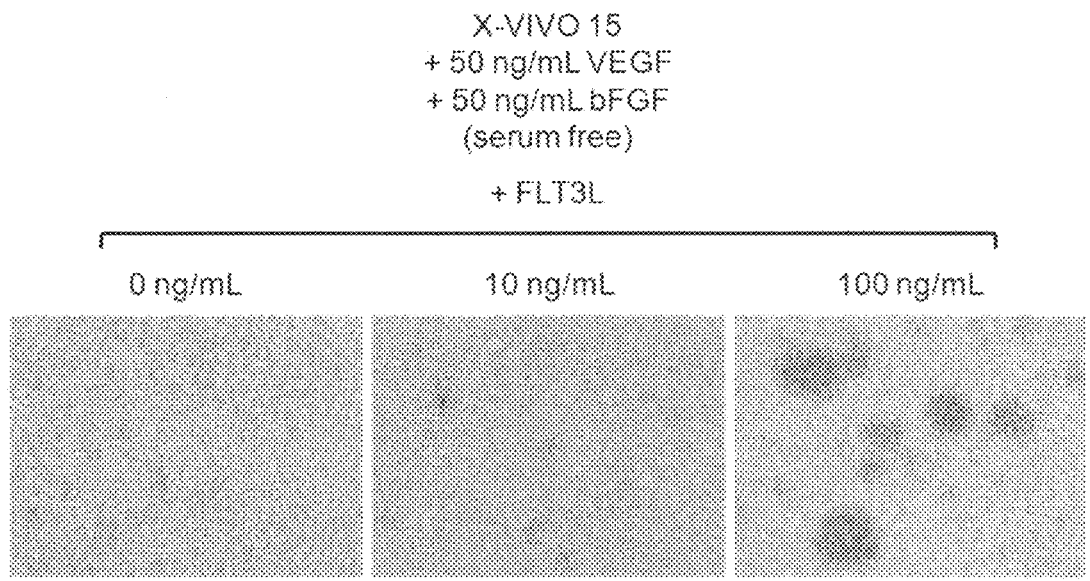
FIG. 13 shows the FLT3L concentration-dependency of differentiation inducing culture of human peripheral blood mononuclear cells in X-VIVO 15 medium supplemented with 50 ng/mL VEGF and 50 ng/mL bFGF.

Human peripheral blood mononuclear cells were cultured with inducing differentiation for one week in X-VIVO 15 medium supplemented with 50 ng/mL VEGF, 50 ng/mL bFGF and 0-100 ng/mL FMS-like tyrosine kinase 3 ligand (FLT3L) in a culture dish. The results confirmed that the number of cell aggregates in semifloating states increases in FLT3L concentration dependent manner (FIG. 13).

(9)

Figure 14:
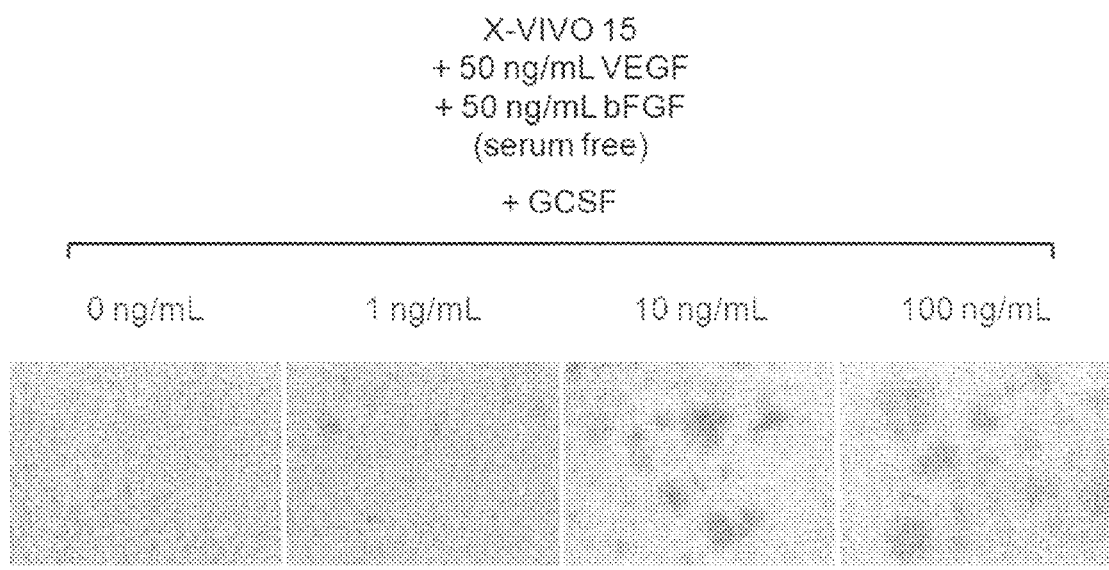
FIG. 14 shows the results of differentiation-inducing culture of human peripheral blood mononuclear cells in X-VIVO 15 medium supplemented with 50 ng/mL VEGF, 50 ng/mL bFGF, and 0-100 ng/mL G-CSF.

Human peripheral blood mononuclear cells were cultured with inducing differentiation for one week in X-VIVO 15 medium supplemented with 50 ng/mL VEGF, 50 ng/mL bFGF and 0-100 ng/mL granulocyte-colony stimulating factor (G-CSF) in a culture dish. The results confirmed that the number of cell aggregates in semifloating states increases in G-CSF concentration dependent manner (FIG. 14).

(10)

Human peripheral blood mononuclear cells were cultured with inducing differentiation for one week in X-VIVO 15 medium supplemented with 50 ng/mL VEGF and 50 ng/mL bFGF, and 0-100 ng/mL TPO in a culture dish. The results confirmed that the number of cell aggregates in semifloating states increases in thrombopoietin (TPO) concentration dependent manner (FIG. 15-1). Also, the number of each size of cell aggregates on the fourth day in culture was measured and analyzed quantitatively. The results indicate that the addition of TPO increases the number of large size cell aggregates, and the tendency of increasing the occurrence of large size cell aggregates was found especially when 10-100 ng/mL was added (FIG. 15-2). Based on this experimental result, the optimal concentration of TPO to be added to medium was considered to be 10-100 ng/mL.

(11)

Figure 16:
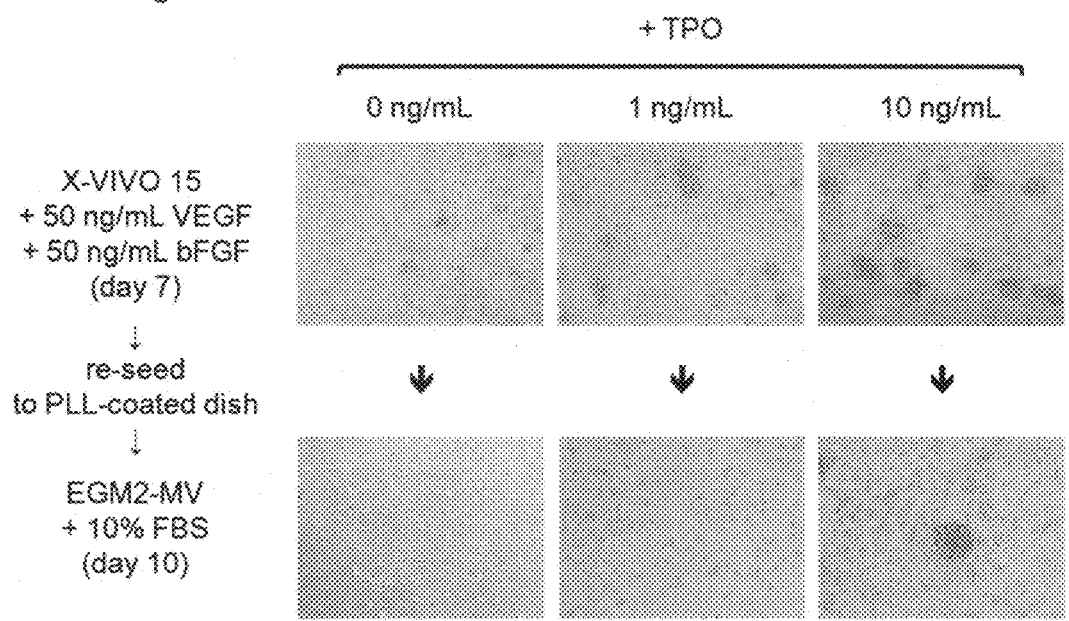
FIG. 16 shows the results of differentiation-inducing culture of human peripheral blood mononuclear cells in X-VIVO 15 medium supplemented with 50 ng/mL VEGF, 50 ng/mL bFGF, and 0-100 ng/mL TPO.

Semifloating cell aggregates obtained by culturing human peripheral blood mononuclear cells with inducing differentiation for one week in X-VIVO 15 medium supplemented with 50 ng/mL VEGF, 50 ng/mL bFGF, and 0-100 ng/mL TPO in a culture dish were collected, and reseeded and cultured for three days in EGM2-MV medium supplemented with 20% FBS in a culture dish treated with PLL. The results confirmed that adherent cells in spindle shape appear, and further that the number of adherent cells after reseeding increases at most in differentiation-inducing culture in the presence of 100 ng/mL TPO (FIG. 16).

(12)

Figure 17:
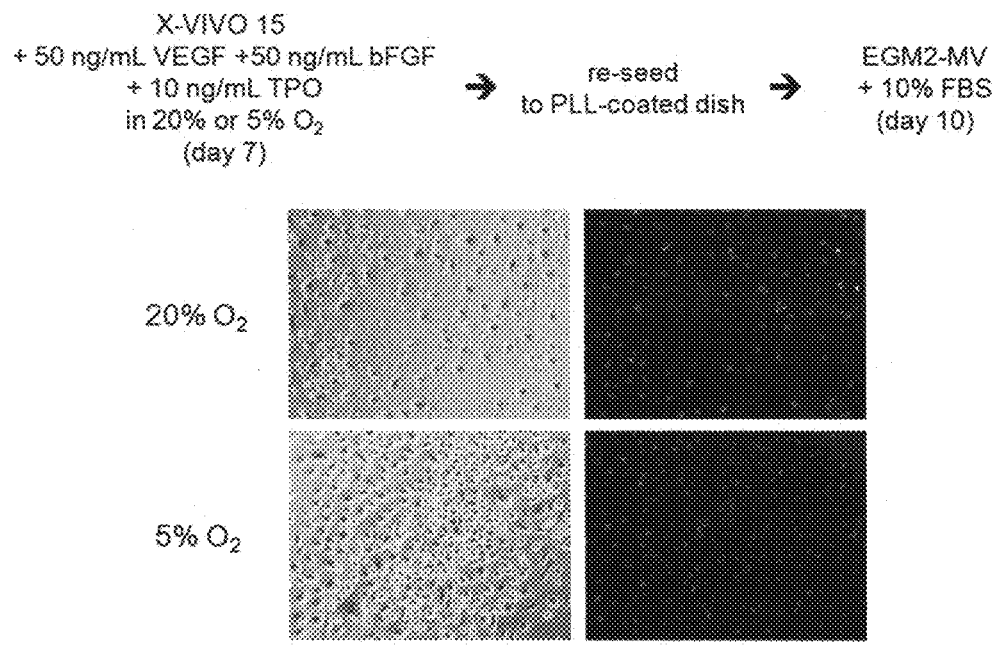
FIG. 17 shows the results of further culture in EGM2-MV medium supplemented with 20% FBS, of cell aggregates obtained by differentiation-inducing culture of human peripheral blood mononuclear cells in X-VIVO 15 medium supplemented with 50 ng/mL VEGF, 50 ng/mL bFGF, and 100 ng/mL TPO.

Semifloating cell aggregates obtained by culturing human peripheral blood mononuclear cells with inducing differentiation for one week in X-VIVO 15 medium supplemented with 50 ng/mL VEGF, 50 ng/mL bFGF, and 100 ng/mL TPO, at 20% or 5% oxygen concentration in a culture dish were collected, and reseeded and cultured for three days in EGM2-MV medium supplemented with 20% FBS in a culture dish treated with PLL. The results confirmed that adherent cells in spindle shape appear and further that these are visualized by uptaking acetylated LDL labeled with DiI. Also, it was confirmed that an initial culture at 5% oxygen concentration (hypoxia culture) increases the number of adherent cells after reseeding (FIG. 17).

(13)

Figure 18:
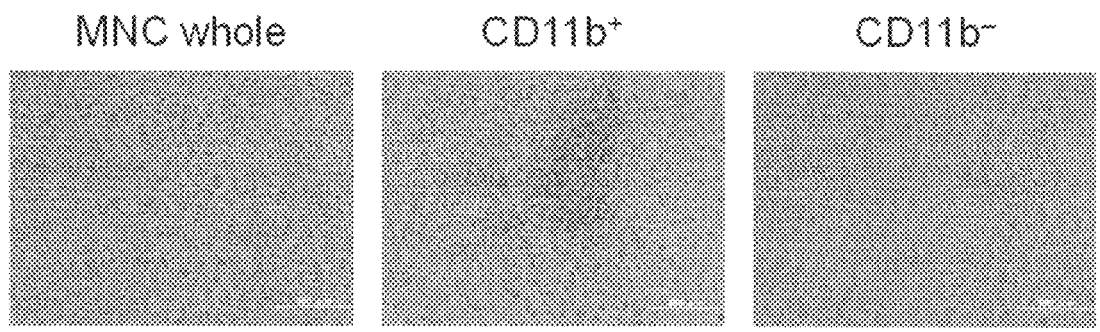
FIG. 18 shows the results of differentiation-inducing culture of peripheral blood mononuclear cells (CD11b-positive/CD11b-negative cells) of a multiple myeloma patient in X-VIVO 15 medium supplemented with 50 ng/mL VEGF and 50 ng/mL bFGF.

Peripheral blood mononuclear cells obtained from a patient with multiple myeloma received the mobilization of precursor cells from bone marrow by administration of G-CSF after chemotherapy, at the time of cell harvest for autologous peripheral stem cell transplantation, CD11b-positive cells and CD11b-negative cells purified with magnetic beads were cultured with inducing differentiation for four days in X-VIVO 15 medium supplemented with 50 ng/mL VEGF and 50 ng/mL bFGF. As a result, the formation of spheroidal cell aggregates was seen at high frequency in CD11b-positive cells (FIG. 18). Also, adherent cells in spindle shape were observed in part.

Discussion:

From the foregoing results, it was suggested that for the induction of differentiation into cells with desired angiogenesis ability, X-VIVO 15 medium is more suitable than the EGM2-MV medium, and that culturing under hypoxia conditions and the addition of bFGF increases cell viability.

Also, it was confirmed that the addition of FLT3L, G-CSF, and TPO (in serum free culture) improves the occurrence of desired angiogenesis ability in a concentration dependent manner. Furthermore, because differentiation-inducing culture under hypoxia conditions increases adherence dramatically in the presence of serum, it is expected that also in vivo, the desired localizing ability to ischemic site etc. increases. In addition, when harvesting peripheral blood mononuclear cells, pre-administration of G-CSF increases the spheroid formation ability and it can be expected that desired blood vessel stabilizing cells are obtained more efficiently.

Even cells that show weak adhesion in a serum free medium can acquire adherence depending on the environment.

Particularly, adherence upon reseeding into serum-containing medium increases dramatically when differentiation is induced under hypoxic conditions (5% $O_2$). However, cells adhered strongly to culture dish are difficult to recover and their viability is not high either. Also, culturing in semifloating states make cell recovery easier.

Further, it was suggested that among the cell population differentiated from mononuclear cells, the CD11b-positive fraction is the main source of early stage adherent cells.

Example 4

Flowcytometry and Quantitative RT-PCR Analysis of CD11b-Positive Fraction of Human Peripheral Blood Mononuclear Cells (1)

Figures 1, 19:
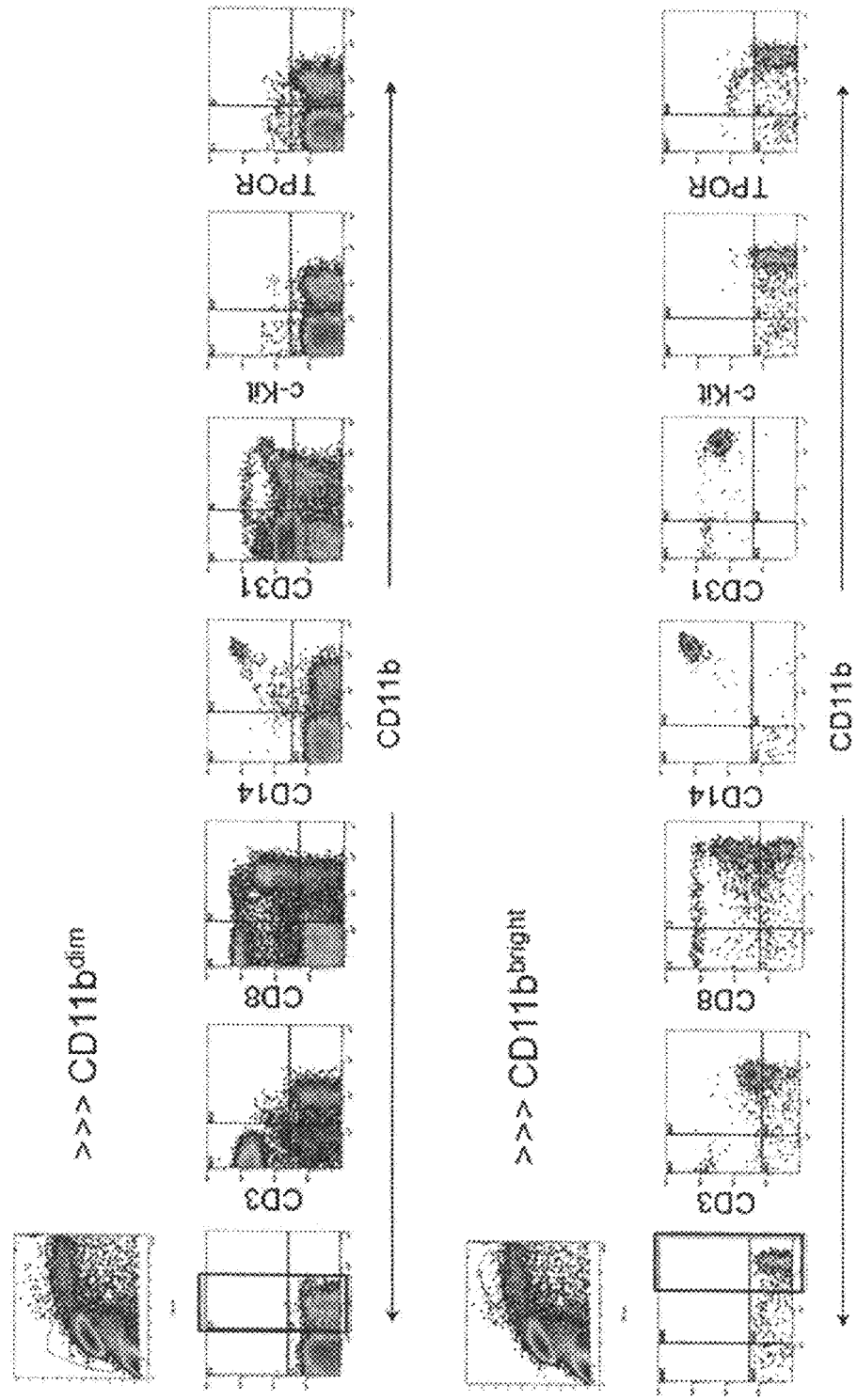
Figures 2, 19:
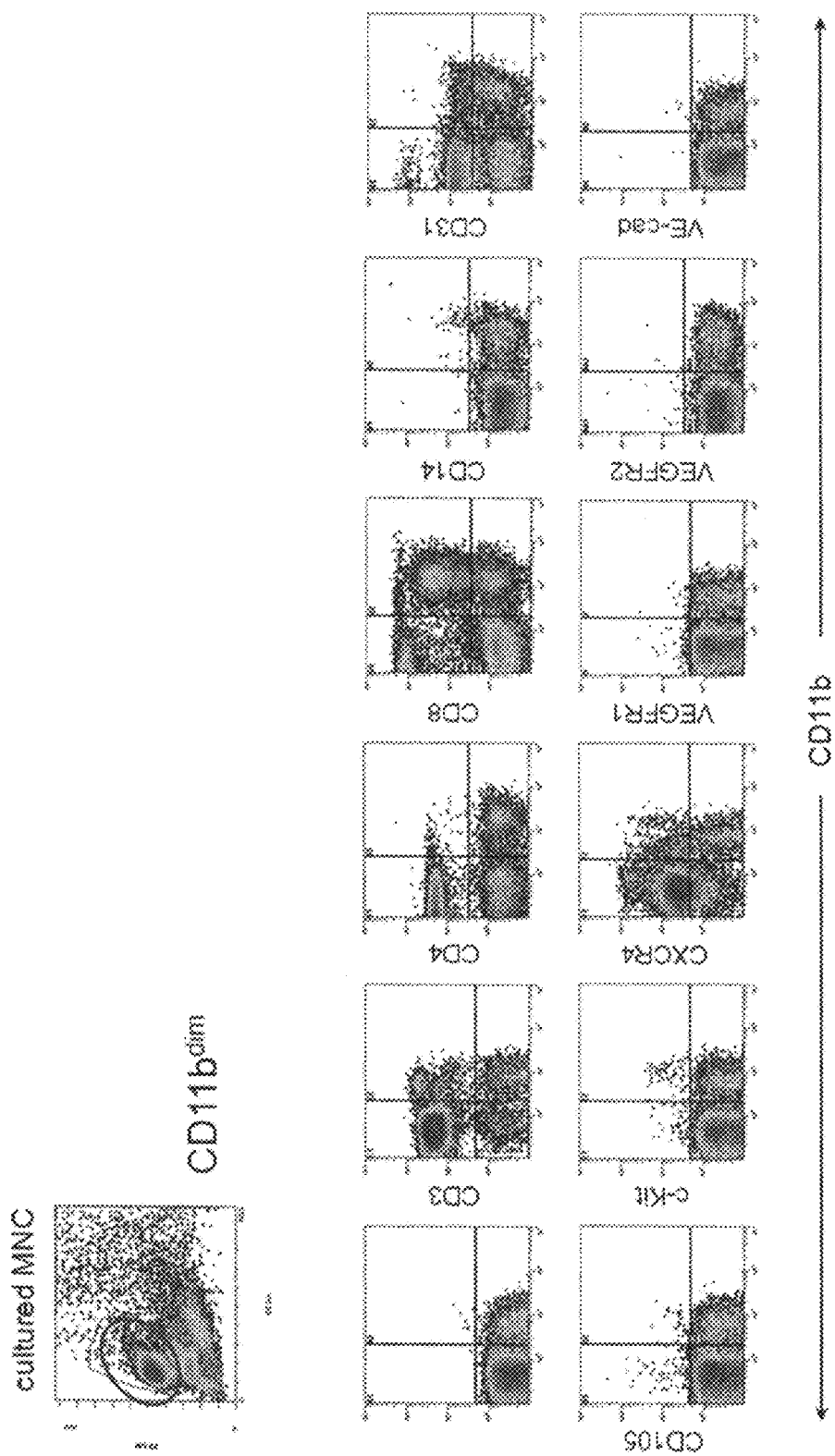
Figures 3, 19:
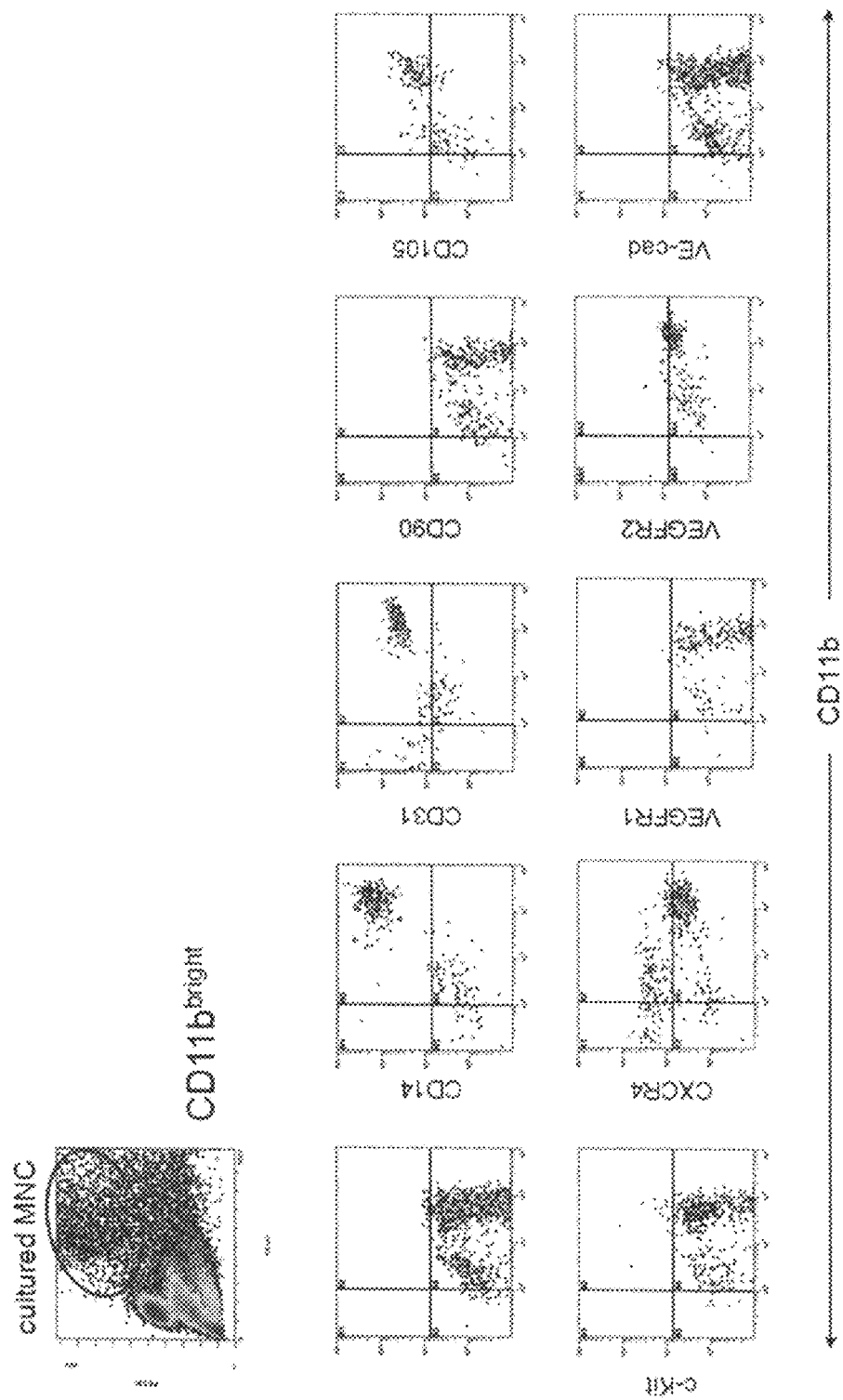
Figures 4, 19:
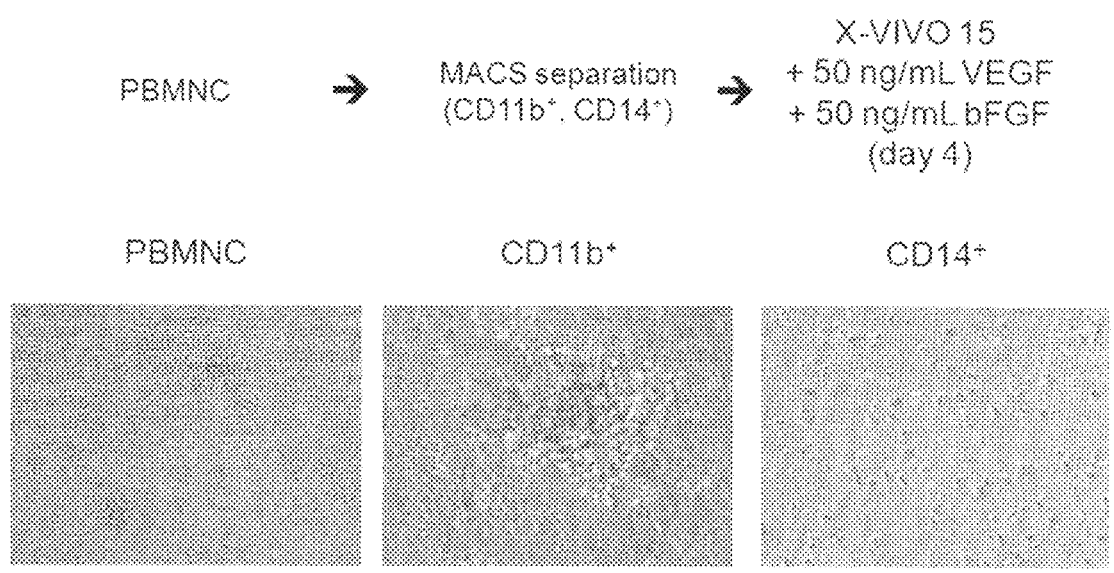
Figures 5, 19:
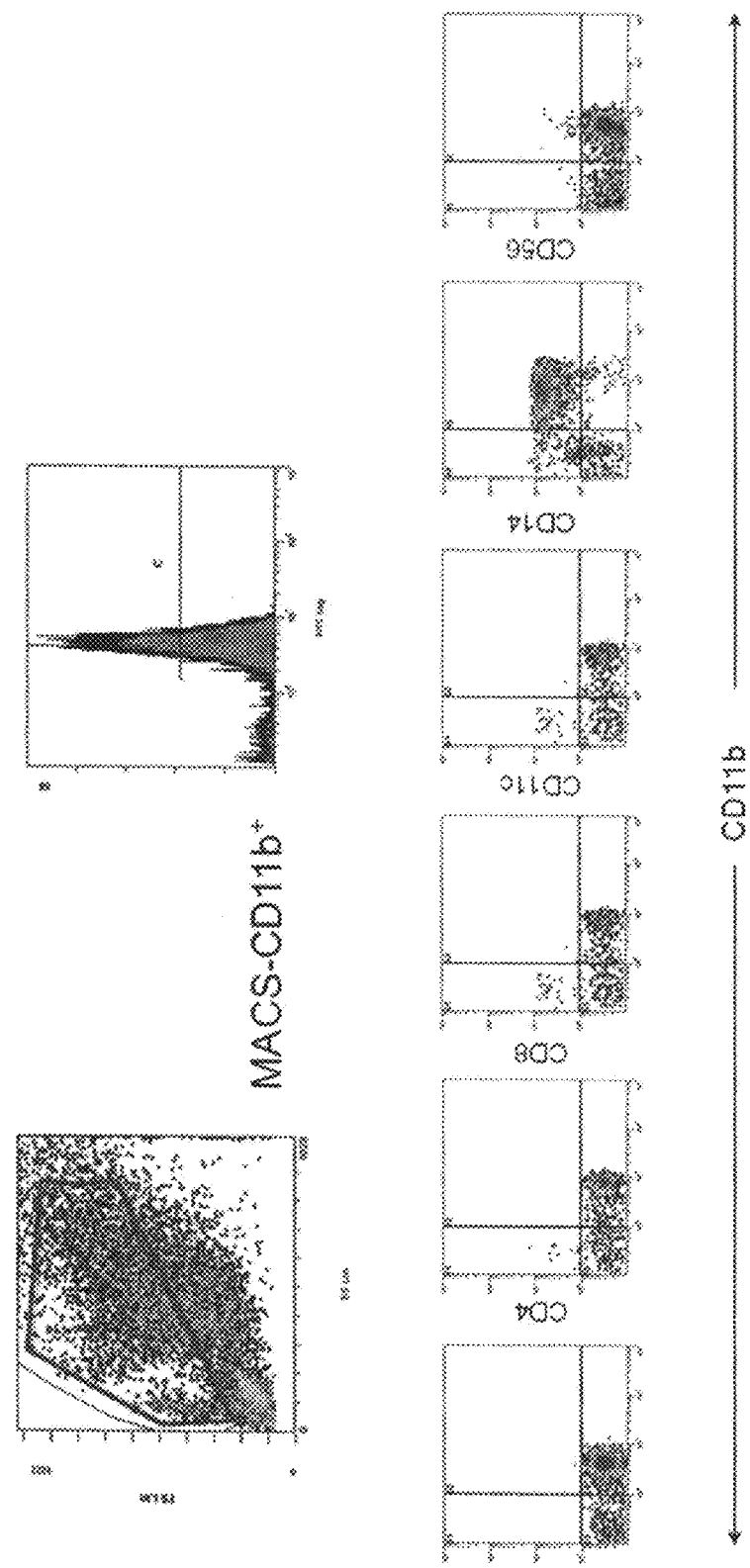

Human peripheral blood mononuclear cells were analyzed by 2 color flowcytometry. The CD11b-positive fraction of human peripheral blood mononuclear cells comprises $CD11b^{dim}$ and $CD11b^{bright}$, the former was $CD31^{dim}/CD14^-$ (mainly lymphocytes), and the latter was $CD31^{bright}/CD14^+$ (mainly monocytes; FIG. 19-1). Note that "dim" means weak immunostaining and relatively little expression of the marker, and "bright" means strong immunostaining and relatively large expression of the marker.

(2)

Human peripheral blood mononuclear cells were cultured with inducing differentiation for four days in X-VIVO 15 medium supplemented with 50 ng/mL VEGF and 50 ng/mL bFGF in a culture dish, and analyzed by 2 color flowcytometry. The $CD11b^{dim}$ fraction expresses CXCR4 and CD31 and c-Kit-positive cells were also detected, though little (FIG. 19-2). Moreover, the $CD11b^{bright}$ fraction expressed CD14, CD31, CD105, and CXCR4, and c-Kit-positive and Flk-1-positive cells were also detected, though little (FIG. 19-3).

Cells obtained by sorting of human peripheral blood mononuclear cells, CD11b-positive cells, or CD14-positive cells with magnetic beads were cultured with inducing differentiation for 4 days in X-VIVO 15 (supplemented with 50 ng/mL VEGF and 50 ng/mL bFGF) without serum. Because the occurrence of semifloating cell aggregates was low when cultured only the CD14-positive fraction ($CD11b^{bright}/CD31^{bright}/CD14^+$), it was expected that in the CD11b-positive fraction of human peripheral blood mononuclear cells, $CD11b^{dim}/CD31^{dim}/CD14^-$ constituted the main cell source of the cell aggregates with a blood vessel stabilization effect due to differentiation-inducing culture, or the presence of $CD11b^{dim}/CD31^{dim}/CD14^-$ is necessary for the differentiation into cells with a blood vessel stabilization effect of $CD11b^{bright}/CD31^{bright}/CD14^+$ (FIG. 19-4).

(3)

Human peripheral blood mononuclear cells were cultured with inducing differentiation for 4 days in X-VIVO 15 (supplemented with 50 ng/mL VEGF and 50 ng/mL bFGF) without serum, and CD11b-positive cells were sorted with magnetic beads. Analysis of surface marker expression of CD11b-positive fraction by 2 color flowcytometry indicated that CD14-positive cells were main constituents (FIG. 19-5).

(4)

Figure 20:
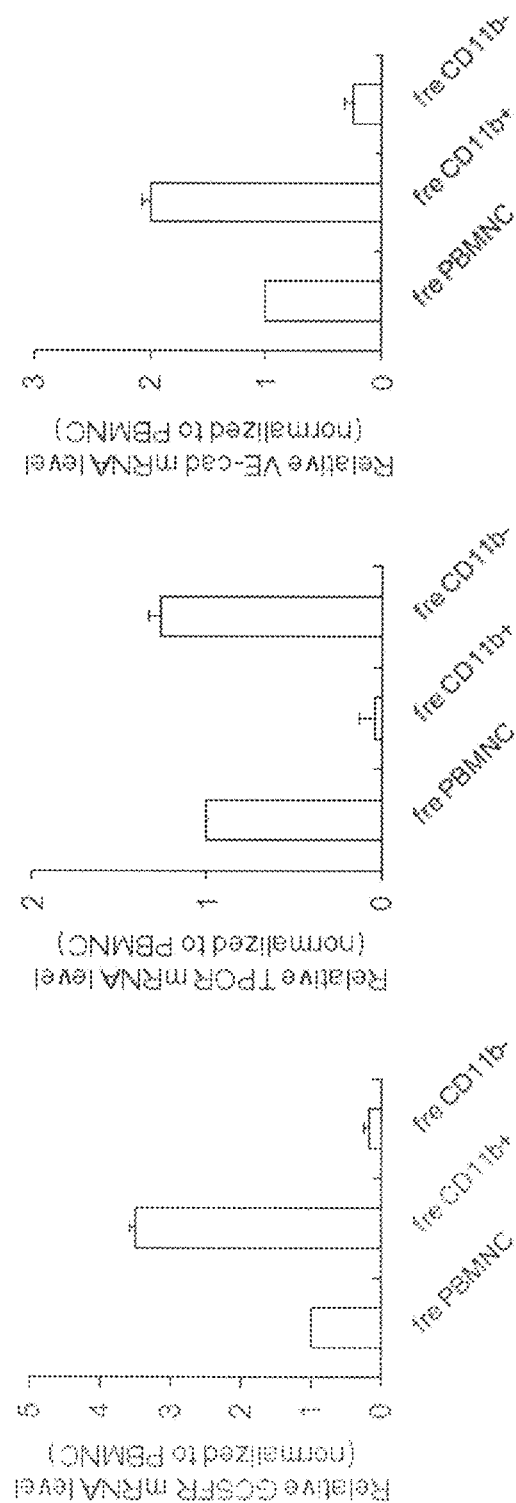
FIG. 20 shows the results of expression analysis of G-CSF receptor, TPO receptor, and VE-cadherin mRNAs in human peripheral blood mononuclear cells (CD11b-positive fraction/CD11b-negative fraction/all mononuclear cells).

The CD11b-positive fraction was purified from human peripheral blood mononuclear cells with magnetic beads, and the expression of G-CSF receptor, TPO receptor and VE-cadherin mRNA in the fraction was analyzed in comparison with the CD11b-negative fraction and all mononuclear cells. The results indicated that the expression of G-CSF receptor and VE-cadherin was higher in the CD11b-positive fraction, while, contrary, the expression of TPO receptor was higher in CD11b-negative fraction (FIG. 20).

(5)

Figures 1, 21:
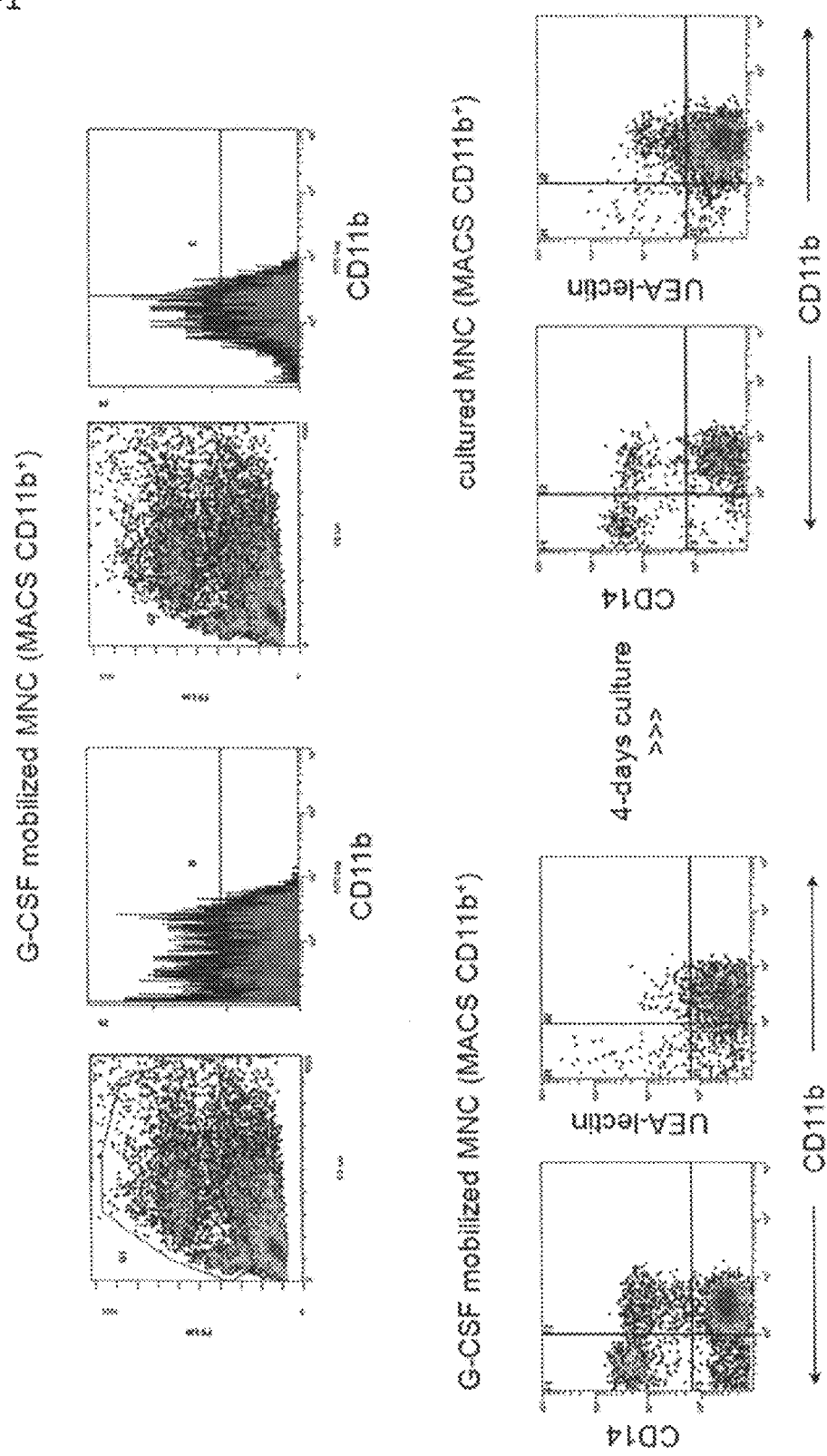
Figures 2, 21:
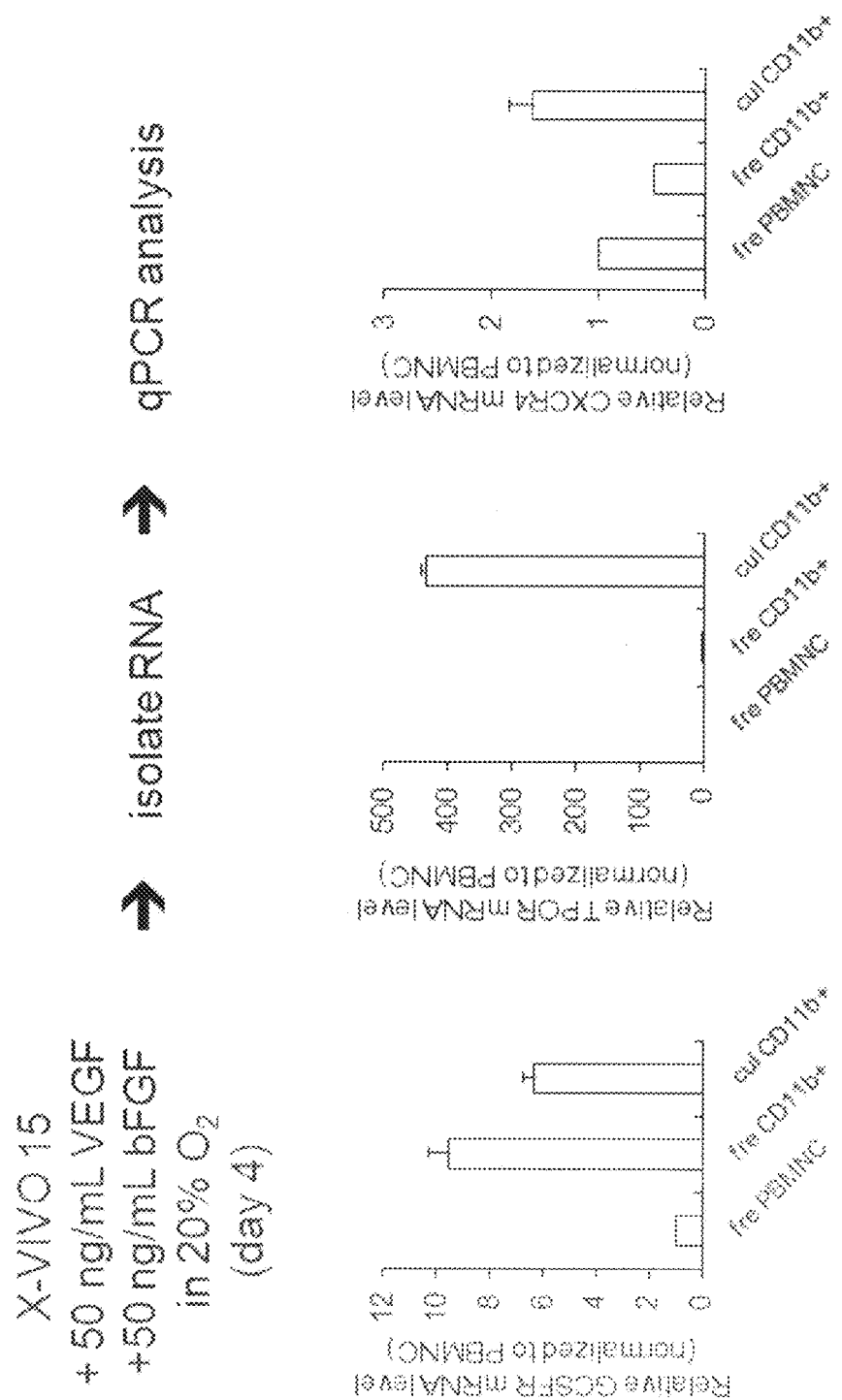

Peripheral blood mononuclear cells of a multiple myeloma patient who received the administration of G-CSF after chemotherapy, recovered at the time of cell harvest for peripheral blood stem cell transplantation, and cells cultured with inducing differentiation for 4 days in X-VIVO 15 (supplemented with 50 ng/mL VEGF and 50 ng/mL bFGF) without serum were sorted with magnetic beads to obtain CD11b-positive cells of each, and the expression of CD14 and the affinity to UEA-lectin of the CD11b-positive fractions were analyzed by 2 color flowcytometry (FIG. 21-1).

(6)

RNA was extracted from each of cells separated as CD11b-positive cells with magnetic bead from peripheral blood mononuclear cells obtained from a patient with multiple myeloma received the mobilization of precursor cells from bone marrow by administration of G-CSF after chemotherapy, at the time of cell harvest for autologous peripheral stem cell transplantation (fresh CD11b$^+$) and cells obtained by culturing these with inducing differentiation for four days in X-VIVO 15 medium supplemented with 50 ng/mL VEGF and 50 ng/mL bFGF and analyzed for TPO receptor mRNA by quantitative RT-PCR. As a result, compared with before culturing, the expression level of the TPO receptor became 100 times or more. In addition, the expression of G-CSF receptor in CD11b-positive cells was remarkably higher compared with the mononuclear cells before the separation, while increase of expression by the differentiation inducing culture was not observed. On the other hand, the expression of CXCR4 in the CD11b-positive cells was increased about three times (FIG. 21-2).

Discussion:

From the foregoing, the possibility was suggested that in the CD11b-positive fractions, the presence of CD11b$^{dim}$/CD31$^{dim}$/CD14$^-$/CXCR4$^+$ or CD11b$^{bright}$/CD14$^+$/CD105$^+$ is important for the induction of differentiation into cell aggregates with a blood vessel stabilizing effect.

The CD11b-positive fraction of peripheral blood mononuclear cells mobilized from bone marrow by the administration of G-CSF was considered to be more desirable as a source of cells for inducing the stabilization of new blood vessels, because the fraction has high colony formation ability in serum free media supplemented with VEGF etc. In addition, increase of localizing ability to ischemia tissue can be expected, because increase of the expression of CXCR4 is found. Further study is required on the meaning of decreases in CD14 expression and increase in affinity to UEA-lectin during the course of the induction of differentiation.

Example 5

Angiogenesis Ability In Vitro and Mouse Limb Ischemia Model Transplantation Experiment (1)

Figure 22:
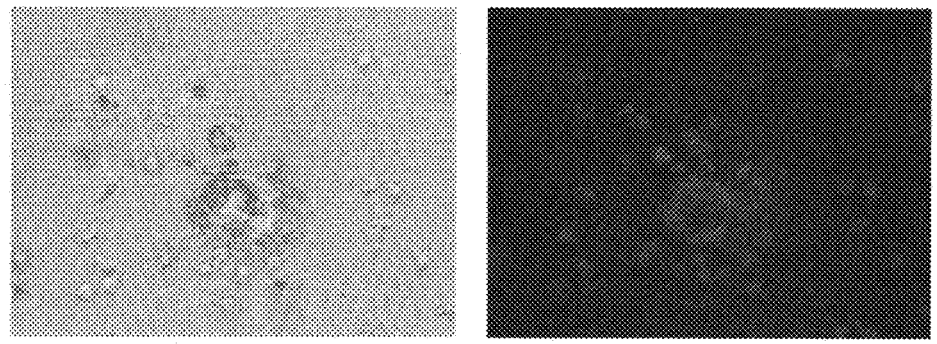
FIG. 22 shows the lumen formation on Matrigel (in culture in EGM2-MV medium supplemented with 10% FBS), of CD11b-positive fraction obtained by differentiation-inducing culture of human peripheral blood mononuclear cells in X-VIVO 15 medium supplemented with 50 ng/mL VEGF, 50 ng/mL bFGF, and 20 ng/mL TPO in culture dish.

Semifloating cell aggregates obtained by culturing human peripheral blood mononuclear cells with inducing differentiation for four days in X-VIVO 15 medium supplemented with 50 ng/mL VEGF and 50 ng/mL bFGF in a culture dish were recovered and purified the CD11b-positive fraction using magnetic beads on which a CD11b antibody was immobilized. This CD11b-positive fraction was allowed to uptake acetylated LDL labeled with DiI, and cultured on Matrigel for 7 days in EGM2-MV medium supplemented with 10% FBS. The results confirmed that the visualized cells form lumens (FIG. 22).

(2)

Spheroidal cell aggregates obtained by culturing human peripheral blood mononuclear cells for four days in X-VIVO 15 (supplemented with 50 ng/mL VEGF and 50 ng/mL bFGF) supplemented with 20 ng/mL TPO were recovered.

Figures 1, 23:
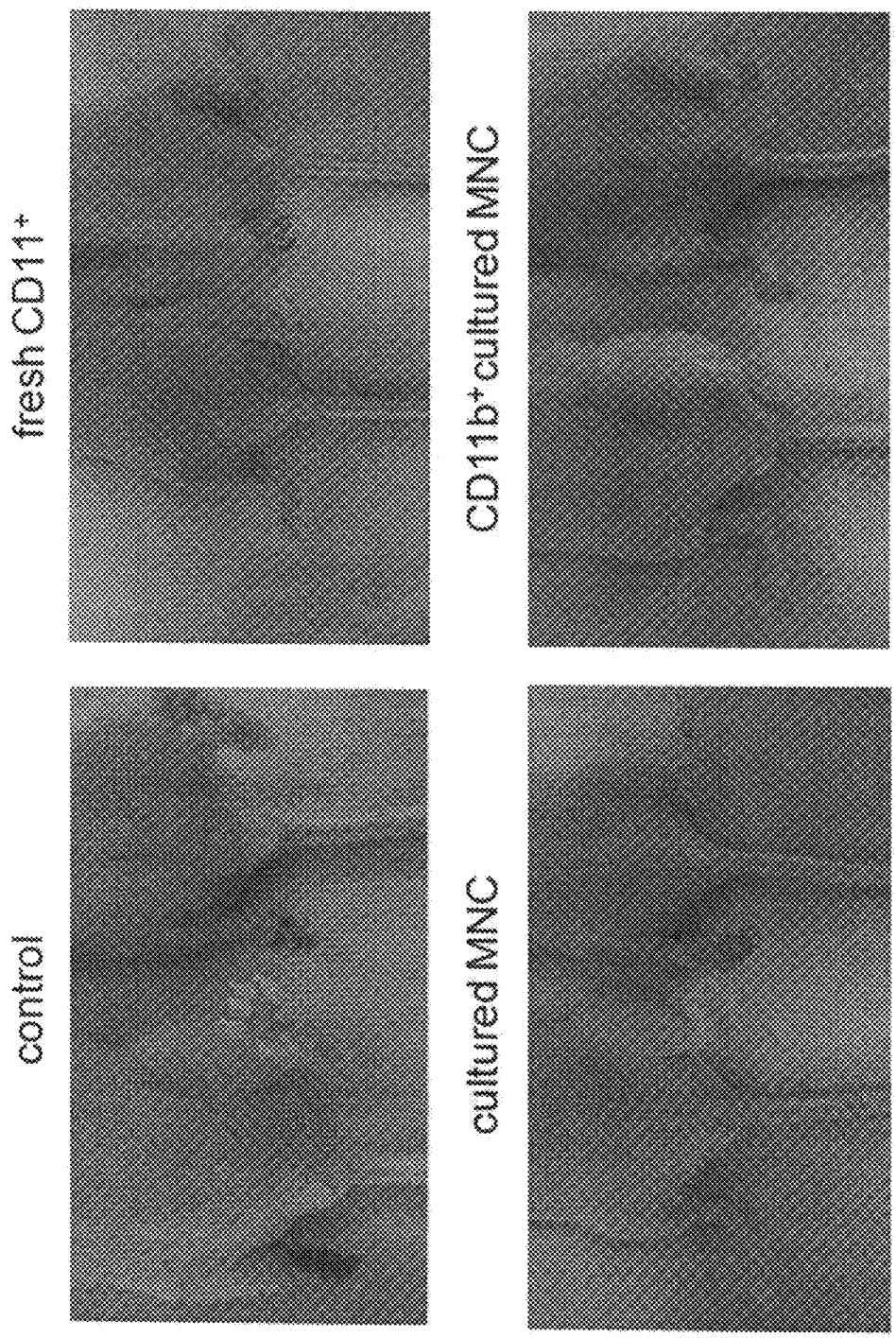
Figures 2, 23:
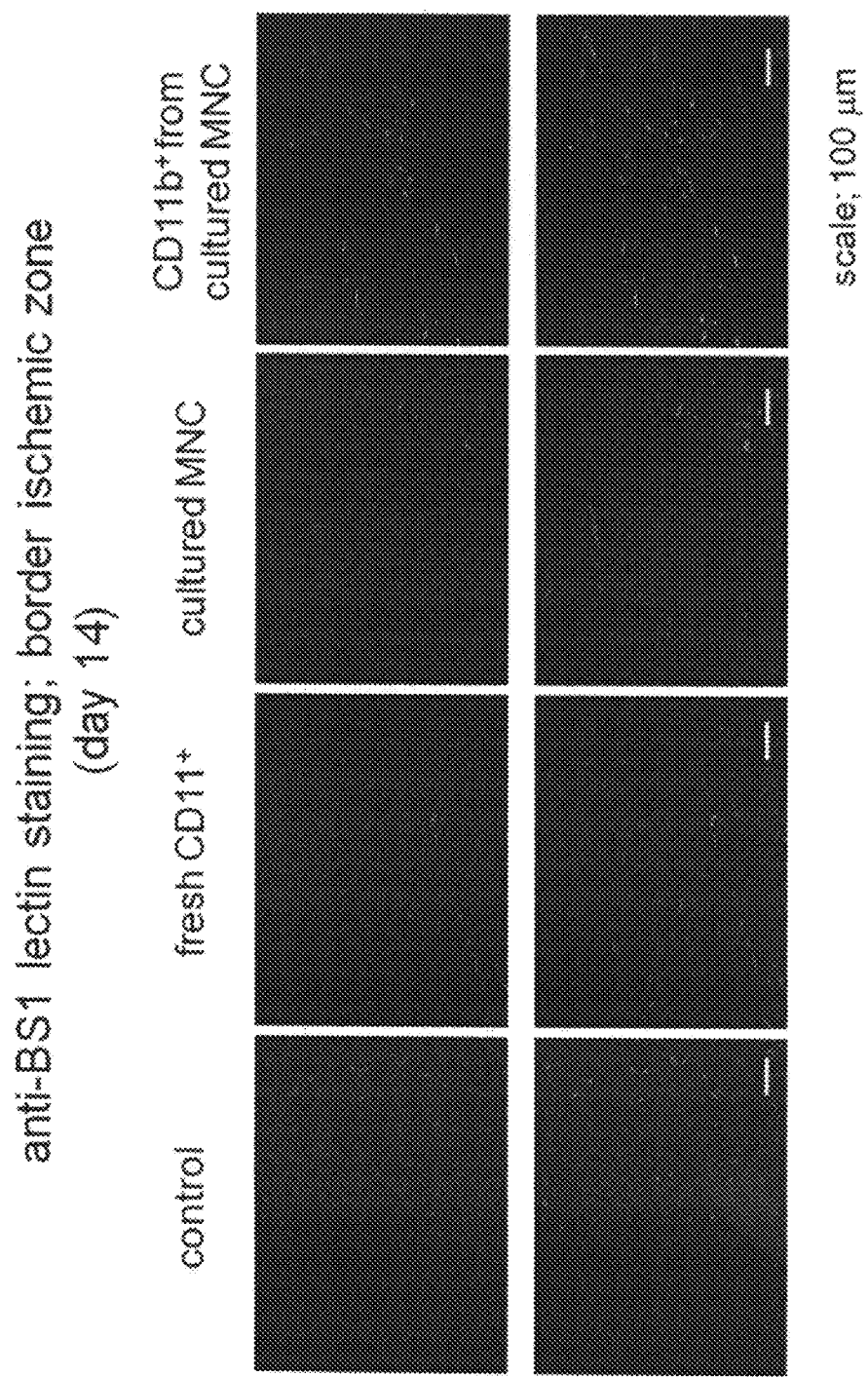
Figures 3, 23:
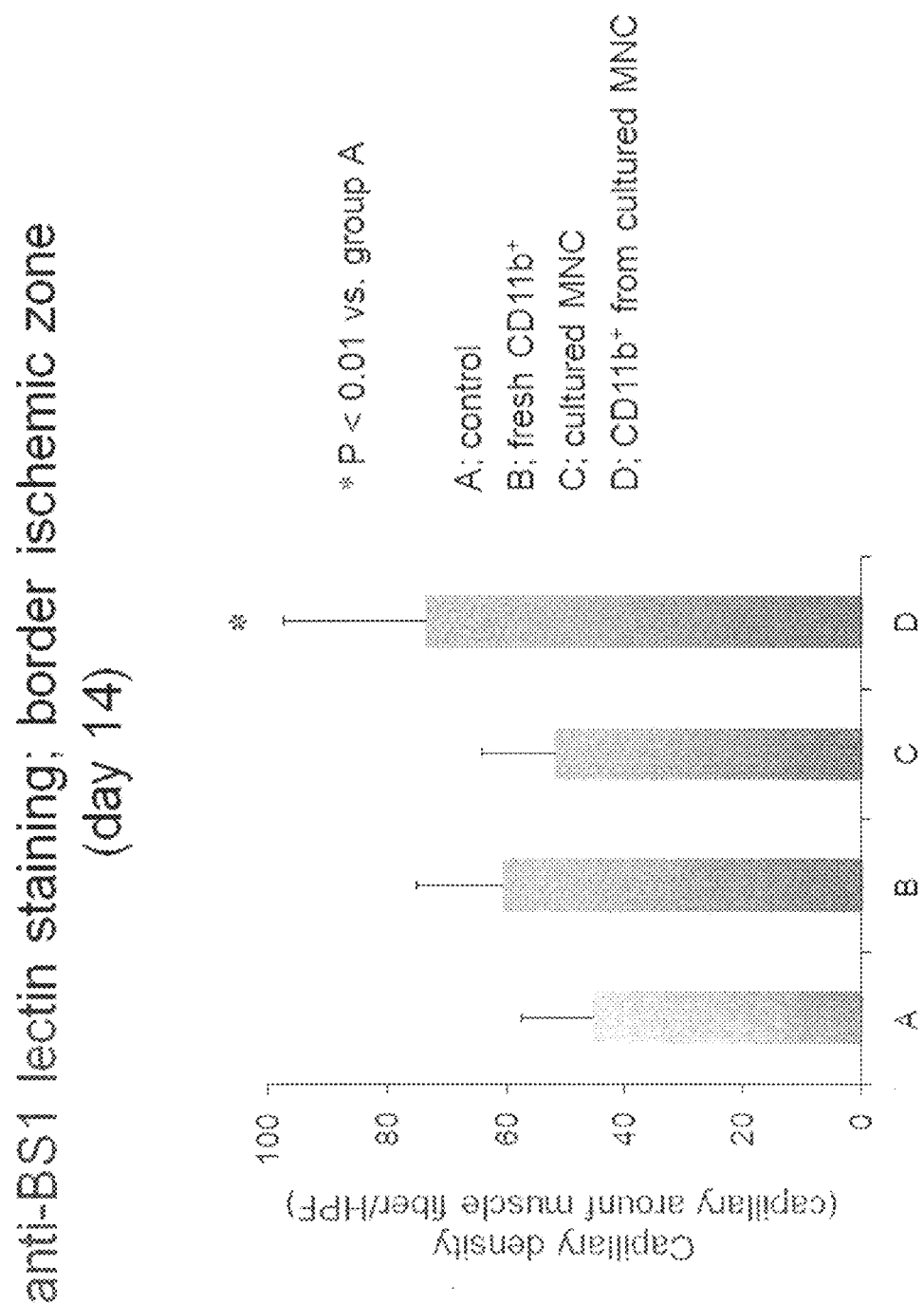

After removing dead cells using magnetic beads labeled with Annexin-V, CD11b-positive cells were purified with magnetic beads (CD11b$^+$ cultured MNC). PBS, CD11b-positive cells without differentiation-inducing culture (fresh CD11b$^+$), mononuclear cell with differentiation-inducing culture (cultured MNC) were used as control. Using eight weeks old, female Balb/c nude mice, Limb ischemia model made by ligating right arteria femoralis at 2 places was made. After three days, $3 \times 10^5$ cells from each population was suspended with Matrigel with low concentrations of growth factors (growth factor reduced matrigel; BD354230). They were divided and locally injected into the ischemia limb at five sites. The photographs of the ischemia limbs and unaffected limbs after two weeks are shown (FIG. 23-1).

Two weeks after the cell transplantation, BS1-lectin was injected into heart. After leaving for five minutes, perfusion fixation was performed using 4% paraformaldehyde and ischemia limbs were recovered. They were postfixed with 4% parafolmaldehyde (for 3 hours, at 4° C.) and embedded in paraffin to make tissue section. Fluorescence microscopy photographs (×20 objective) are shown (FIG. 23-2: lower panels show merge images with nuclear staining with DAPI. scale bar, 100 µm), in which reactive angiogenesis (functional blood vessel) was immunohistologically detected with an anti-BS1-lectin antibody in the border ischemic zone (near the area where inflammatory cell infiltration due to ischemia is found).

The functional blood vessels visualized with BS1-lectinin in the border ischemic zone were quantified using ImageJ software. Microvessels along muscle fibers are counted and the blood vessel density was calculated (FIG. 23-3).

In the end, foot necrosis associated with ischemia was found in all cases (8/8) in control (transplantation of Matrigel), while limbs shortening associated with foot necrosis was circumvented in all individuals in the treated group (0/6). On the other hand, transplantation of $3 \times 10^5$ cells into limbs ischemia mouse using CD11b positive cells purified with magnetic beads from human peripheral-blood mononuclear cells (fresh CD11b$^+$) or cells obtained by removing dead cells from semifloating cell aggregates obtained by culturing human peripheral blood mononuclear cells with inducing differentiation for four days in X-VIVO 15 medium supplemented with 50 ng/mL VEGF, 50 ng/mL bFGF and 20 ng/mL TPO in a culture dish (cultured MNC) had no observed effect of improving from ischemia.

(3)

CD11b-positive cells purified with magnetic beads (CD11b$^+$ from cultured MNC), CD11b-positive cells without differentiation-inducing culture (fresh CD11b$^+$), mononuclear cells with differentiation-inducing culture (cultured MNC), Matrigel (control) were transplanted into limb ischemia mouse according to the above method, and the blood flow evaluation (improvement rate in ischemia limb/unaffected limb ratio just after treatment) by the laser Doppler was conducted 14 days after the ligation in limb.

The results: control group (n=11), 22.6±8.3%; CD11b-positive cell transplantation group without differentiation-inducing culture (n=7), 29.8±6.9%; mononuclear cell transplantation group with differentiation inducing culture (n=7), 27.9±5.7%; vs. CD11b-positive cell transplantation group (n=8), 42.6±10.9% indicated significant enhancement of recovery from limb ischemia (FIG. 25).

Discussion:

The foregoing results confirmed that compared with the angiogenesis ability of human peripheral blood mononuclear cells (including CD11b-positive cell population) as they are, CD11b-positive cell population differentiated from these cells have ability to enhance the structural and functional stabilization of new blood vessels, and can lead to profound recovery from limb ischemia.

Example 6

Gene Expression Analysis by Quantitative RT-PCR in CD11b-Positive Cells Derived from Peripheral Mononuclear Cells from Multiple Myeloma Patient A fraction of peripheral blood mononuclear cells of a multiple myeloma patient who received the administration of G-CSF after chemotherapy, recovered at the time of cell harvest for peripheral blood stem cell transplantation, from which CD11b-positive cells were purified with magnetic beads (fre CD11b), and these CD11b-positive cells were cultured with inducing differentiation for 4 days in X-VIVO 15 medium supplemented with 50 ng/mL VEGF and 50 ng/mL bFGF in 20% oxygen (cul CD11b in 20% $O_2$), or in 5% oxygen (cul CD11b in 20% $O_2$).

Figure 24:
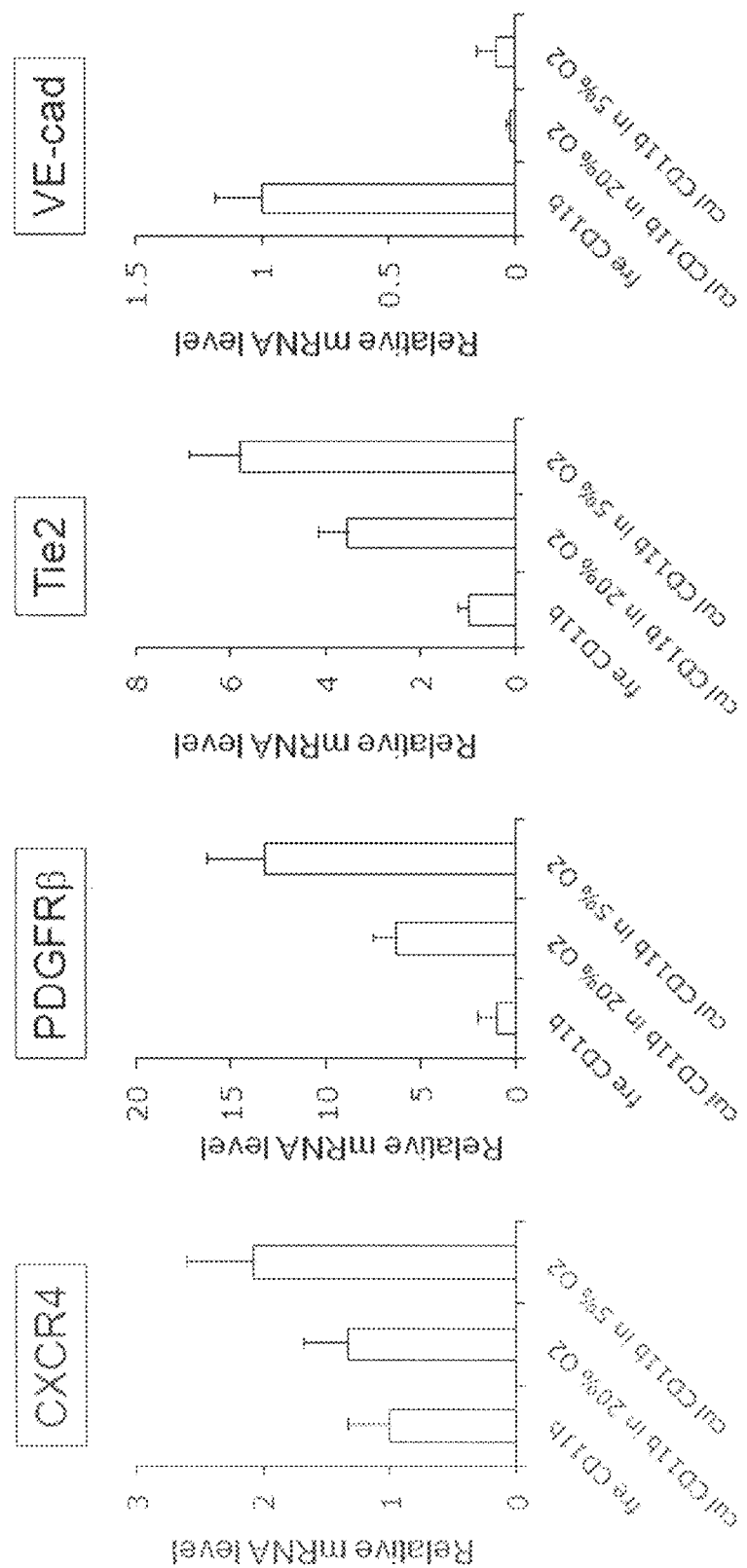
FIG. 24 shows blood flow evaluation (improvement rate in ischemia limb/unaffected side limb ratio just after treatment) results by laser Doppler (nude mouse lower limb ischemia model examination). In the graph, from the left, Matrigel transplantation group (control), CD11b-positive cell transplantation group without differentiation-inducing culture (fresh CD11b$^+$), mononuclear cell transplantation group with differentiation-inducing culture (cultured MNC), CD11b-positive cell transplantation group purified with magnetic beads (CD11b$^+$ from cultured MNC).

Analysis of gene expression in each fraction by quantitative RT-PCR by TaqMan method indicated that during four days of culturing, the expression of CXCR4, PDGFRbβ, and Tie2 was increased and this induction was more enhanced by culturing under the hypoxia environment (FIG. 24). Increase in expression of VE-cadherin was not observed.

Discussion:

From this, it is suggested that especially differentiation-inducing culture under the hypoxia environment enhances differentiation of peripheral blood CD11b-positive mononuclear cells mobilized from bone marrow into pericytes involved in the stabilization of new blood vessels. Moreover, because the culture increases the expression of CXCR4 and Tie2, it is considered that accumulating ability to cancer microenvironment is increased, in which SDF-1, Angiopoietin-1, and Angiopoietin-2 are produced, and further that after localizing such sites, the activation by these ligands become easier.

All the publications, patents, and the patent applications cited herein are incorporated herein by reference in their entireties.

INDUSTRIAL APPLICABILITY

The cell populations according to the present invention are obtained by inducing differentiation, under conditions without animal serum, of mononuclear cells as a source, which can be relatively easily collected from patient's peripheral blood. Therefore, the cell population according to the present invention is free from risk of infection, and it is useful as a clinically applicable and safe cell preparation. Moreover, the invention is useful as an alternative method of conventional vessel regeneration treatments using rare (hematopoietic) stem cells.

The invention claimed is:

1. A diagnostic agent for cancer localization, comprising a cell population with a revascularization ability, expressing CD11b, CD31, CXCR4, CD14, CD105, CD146, VEGF receptor 2, and G-CSF receptor, obtained by inducing differentiation of a mononuclear cell population by culturing the mononuclear cell population in a serum free medium containing one or more selected from vascular endothelial growth factor (VEGF), basic fibroblast growth factor (bFGF), thrombopoietin (TPO), granulocyte-colony stimulating factor (G-CSF) and FMS-like tyrosine kinase 3 ligand (FLT3L), wherein:
the mononuclear cell population is a human mononuclear cell population; and
the cell population with the revascularization ability, expressing CD11b, CD31, CXCR4, CD14, CD105, CD146, VEGF receptor 2, and G-CSF receptor, has selective tropism to one or more of tumor tissue or ischemic zones.

2. A method of preparing a cell population with a revascularization ability, expressing CD11b, CD31, CXCR4, CD14, CD105, CD146, VEGF receptor 2, and G-CSF receptor, comprising the steps of:
1) culturing a mononuclear cell population in a serum-free medium containing one or more selected from vascular endothelial growth factor (VEGF), basic fibroblast growth factor (bFGF), thrombopoietin (TPO), granulocyte-colony stimulating factor (G-CSF) and FMS-like tyrosine kinase 3 ligand (FLT3L), thereby inducing differentiation of the mononuclear cell population, wherein the mononuclear cell population is a human mononuclear cell population; and
2) collecting a cell population expressing CD11b from cell clusters resulting from the culturing, thereby obtaining the cell population with the revascularization ability, expressing CD11b, CD31, CXCR4, CD14, CD105, CD146, VEGF receptor 2, and G-CSF receptor.

3. The method according to claim 2, wherein the cell population is obtained as a semifloating cell population.

4. The method according to claim 3, wherein the culturing is carried out under hypoxia conditions.

5. The method according to claim 4, wherein the hypoxia conditions are conditions that the oxygen concentration is 1-10%.

6. The method according to claim 2, wherein the culturing is carried out in a medium containing VEGF, bFGF and TPO.

7. The method according to claim 2, wherein the mononuclear cell population is prepared by density gradient centrifugation.

8. The method according to claim 2, wherein the cell population with the revascularization ability, expressing CD11b, CD31, CXCR4, CD14, CD105, CD146, VEGF receptor 2, and G-CSF receptor, is obtained as a weakly adhesive and semi-floating cell population and becomes spindle shaped adherent cells.

9. A cell population with a revascularization ability, expressing CD11b, CD31, CXCR4, CD14, CD105, CD146, VEGF receptor 2, and G-CSF receptor, obtained by inducing differentiation of a mononuclear cell population by culturing the mononuclear cell population in a serum free medium containing one or more selected from vascular endothelial growth factor (VEGF), basic fibroblast growth factor (bFGF), thrombopoietin (TPO), granulocyte-colony stimulating factor (G-CSF) and FMS-like tyrosine kinase 3 ligand (FLT3L), wherein the mononuclear cell population is a human mononuclear cell population.

10. The cell population according to claim 9, wherein the cell population is obtained as a semifloating cell population.

11. The cell population according to claim 9, wherein the mononuclear cell population is derived from peripheral blood, bone marrow or umbilical cord blood.

12. The cell population according to claim 9, wherein the culturing is carried out under hypoxia conditions.

13. The cell population according to claim 12, wherein the hypoxia conditions are conditions that the oxygen concentration is 1-10%.

14. The cell population according to claim 9, wherein the culturing is carried out in a medium containing VEGF, bFGF and TPO.

15. The cell population according to claim 14, having the revascularization ability through promotion of neovascular stabilization or maturation.

16. A cell preparation for revascularization treatment, comprising the cell population according to claim 9.

17. The cell preparation according to claim 16, having an anti-ischemia and/or vascular maturation effect.

18. The cell population according to claim 9, wherein the mononuclear cell population is prepared by density gradient centrifugation.

19. The cell population according to claim 9, wherein the cell population is obtained as a weakly adhesive and semi-floating cell population and becomes spindle shaped adherent cells.

* * * * *

UNITED STATES PATENT AND TRADEMARK OFFICE
CERTIFICATE OF CORRECTION

PATENT NO. : 8,951,795 B2  
APPLICATION NO. : 13/138835  
DATED : February 10, 2015  
INVENTOR(S) : Mizukami et al.

It is certified that error appears in the above-identified patent and that said Letters Patent is hereby corrected as shown below:

In the specification:

Column 3, line 63, the text "20.01" should read --2001--.

Column 17, line 19, the text "4-0.7" should read --4-7--.

Signed and Sealed this  
Thirtieth Day of June, 2015

Michelle K. Lee  
*Director of the United States Patent and Trademark Office*